(12) United States Patent
Yan et al.

(10) Patent No.: US 12,064,473 B2
(45) Date of Patent: Aug. 20, 2024

(54) CANCER VACCINES TARGETING SURVIVIN AND USES THEREOF

(71) Applicant: Inovio Pharmaceuticals, Inc., Plymouth Meeting, PA (US)

(72) Inventors: Jian Yan, Wallingford, PA (US); Anna Slager, Lansdale, PA (US); Bradley Garman, Glenside, PA (US); Neil Cooch, Oreland, PA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 1114 days.

(21) Appl. No.: 16/219,520

(22) Filed: Dec. 13, 2018

(65) Prior Publication Data

US 2019/0175707 A1    Jun. 13, 2019

Related U.S. Application Data

(60) Provisional application No. 62/598,267, filed on Dec. 13, 2017.

(51) Int. Cl.
| | | |
|---|---|---|
| *G01N 31/00* | (2006.01) | |
| *A61K 39/00* | (2006.01) | |
| *A61K 39/39* | (2006.01) | |
| *A61P 35/00* | (2006.01) | |
| *C07K 16/40* | (2006.01) | |
| *C12N 15/52* | (2006.01) | |
| *C12N 15/62* | (2006.01) | |
| *G01N 33/53* | (2006.01) | |

(52) U.S. Cl.
CPC ........ *A61K 39/00115* (2018.08); *A61K 39/39* (2013.01); *A61P 35/00* (2018.01); *C07K 16/40* (2013.01); *C12N 15/52* (2013.01); *C12N 15/62* (2013.01); A61K 2039/53 (2013.01); A61K 2039/55527 (2013.01); A61K 2039/575 (2013.01)

(58) Field of Classification Search
None
See application file for complete search history.

(56) References Cited

U.S. PATENT DOCUMENTS

| | | |
|---|---|---|
| 2002/0123099 A1 | 9/2002 | Weiner et al. |
| 2016/0331844 A1 | 11/2016 | Fotin-Mleczek et al. |

FOREIGN PATENT DOCUMENTS

| | | | |
|---|---|---|---|
| WO | 2013151672 A2 | 10/2013 | |
| WO | 2016/170176 A1 | 10/2016 | |
| WO | 2016179573 A1 | 11/2016 | |
| WO | 2017048850 A1 | 3/2017 | |
| WO | WO-2017048850 A1 * | 3/2017 | ............. A61K 39/00 |

OTHER PUBLICATIONS

International Search Report and Written Opinion issued in PCT/US18/65529, dated Aug. 27, 2019.
Seledtsov; "Xenovaccinotherapy for Cancer Treatment"; Siberian Journal of Oncology; vol. 39; 2010; p. 48-57(English Abstract).
Ferlazzo et al.; "Distinct roles of IL-12 and IL-15 in human natural killer cell activation by dendritic cells from secondary lymphoid organs"; PNAS; vol. 101 No. 47; Nov. 2004; p. 16606-16611.
Barrett et al.; "Threonine 48 in the BIR domain of surviving is critical to its mitotic and anti-apoptotic activities and can be phosphorylated by CK2 in vitro"; Cell Cycle; vol. 10 No. 3; 2011; p. 538-548.

* cited by examiner

*Primary Examiner* — Lisa V Cook
(74) *Attorney, Agent, or Firm* — BakerHostetler

(57) ABSTRACT

Disclosed herein are nucleic acid molecules comprising one or more nucleic acid sequences that encode synthetic consensus Survivin antigens. Vectors, compositions, and vaccines comprising one or more nucleic acid sequences that encode synthetic consensus Survivin antigens are disclosed. Methods of treating a subject with a Survivin-expressing tumor and methods of preventing a Survivin-expressing tumor are disclosed. Synthetic consensus Survivin antigens are disclosed.

2 Claims, 17 Drawing Sheets

Specification includes a Sequence Listing.

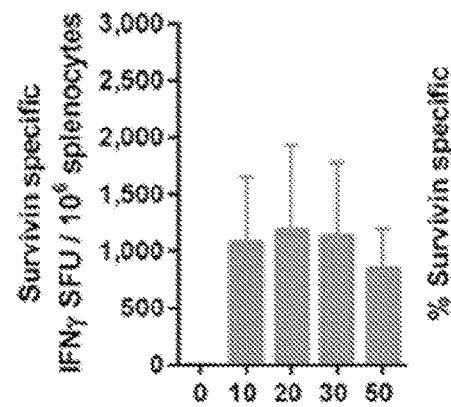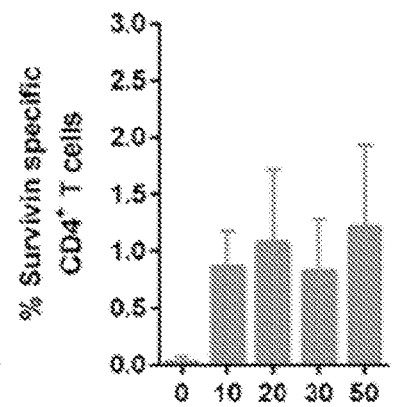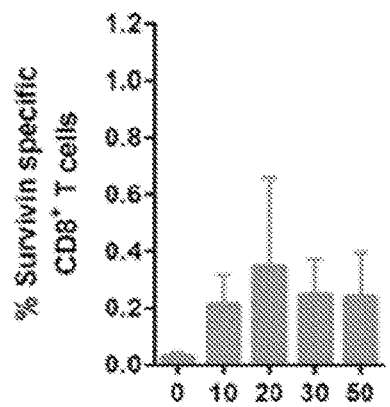
FIG. 7A  FIG. 7B  FIG. 7C
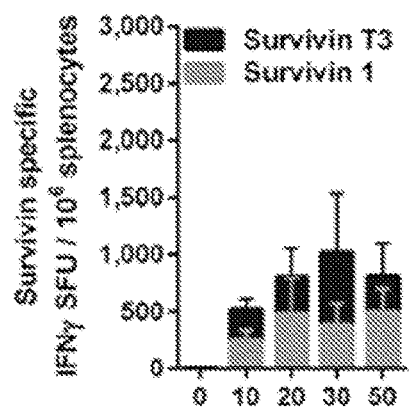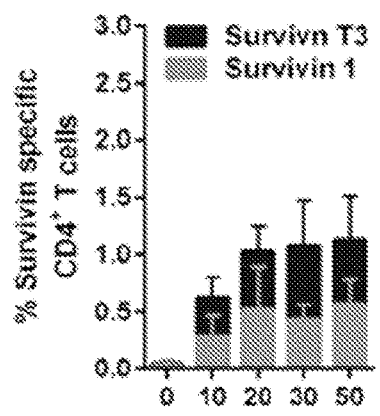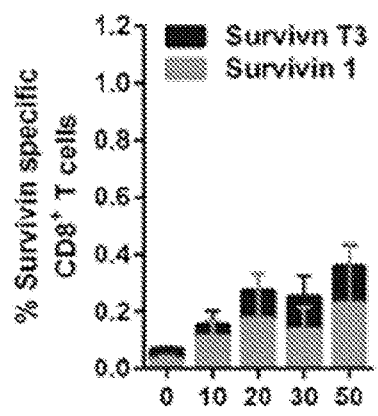
FIG. 7D  FIG. 7E  FIG. 7F

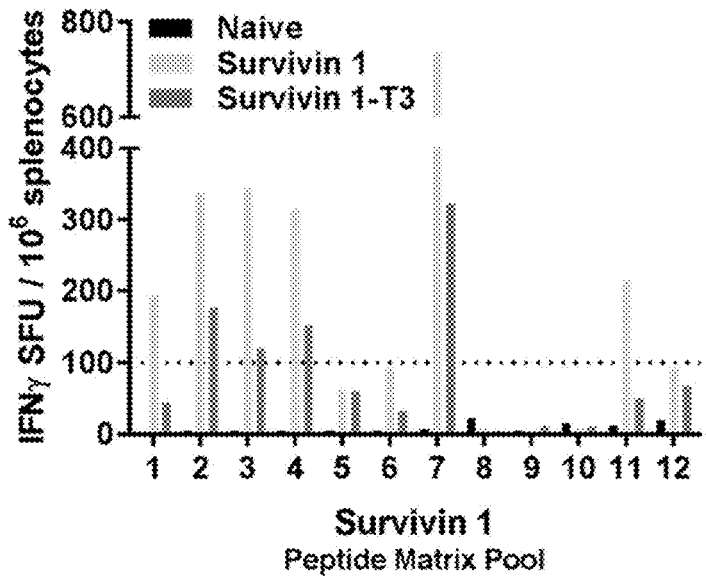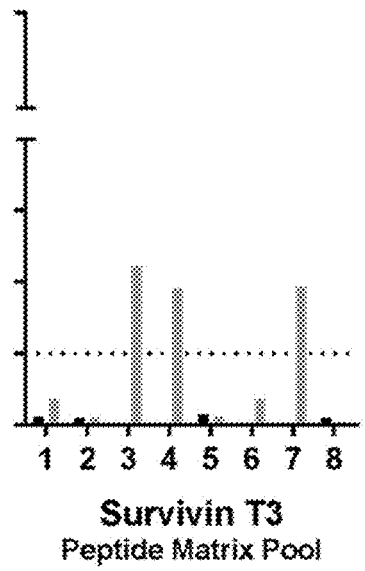
FIG. 11A  FIG. 11B
FIG. 11C
FIG. 11D

United States Patent

SEQUENCE LISTING

<160> NUMBER OF SEQ ID NOS: 13

<210> SEQ ID NO 1
<211> LENGTH: 483
<212> TYPE: DNA
<213> ORGANISM: Artificial Sequence
<220> FEATURE:
<223> OTHER INFORMATION: Synthetic Consensus Survivin isoform 1 DNA
      Coding Sequence pGX1428

<400> SEQUENCE: 1

```
atggattgga cctggattct gttcctggtg gcagcagcaa cccgggtgca ctccggagcc      60
cccacactgc cccctgcctg gcagctgttt ctgaaggacc acaggatctc tacattcaag     120
aactggccct tctggagggg atgcgcatgt gcacctgaga ggatggcaga ggcaggcttc     180
atccactgcc ctgccgagaa tgagccagat ctggcccagt gcttcttttg ttttaaggag     240
ctggagggct gggagccaga cgatgacccc atcgaggagc acaagaagca cagctccggc     300
gccgccttcc tgtctgtgaa gaagcagttt gaggagctga ccctgagcga gttcctgaag     360
ctggatcggg agagagccaa gaacaagatc gccaaggaga ccaacaacaa gaagaaggag     420
tttgaggaga cagccaagaa ggtgaggtgt gccatcgagc agctggccgc catggactga     480
```

```
taa                                                                     483
```

<210> SEQ ID NO 2
<211> LENGTH: 159
<212> TYPE: PRT
<213> ORGANISM: Artificial Sequence
<220> FEATURE:
<223> OTHER INFORMATION: Synthetic Consensus Survivin isoform 1 Protein
      Coding Sequence pGX1428

<400> SEQUENCE: 2

```
Met Asp Trp Thr Trp Ile Leu Phe Leu Val Ala Ala Thr Arg Val
1               5                   10                  15

His Ser Gly Ala Pro Thr Leu Pro Pro Ala Trp Gln Leu Phe Leu Lys
                20                  25                  30

Asp His Arg Ile Ser Thr Phe Lys Asn Trp Pro Phe Leu Glu Gly Cys
            35                  40                  45

Ala Cys Ala Pro Glu Arg Met Ala Glu Ala Gly Phe Ile His Cys Pro
        50                  55                  60

Ala Glu Asn Glu Pro Asp Leu Ala Gln Cys Phe Phe Cys Phe Lys Glu
65                  70                  75                  80

Leu Glu Gly Trp Glu Pro Asp Asp Asp Pro Ile Glu Glu His Lys Lys
                85                  90                  95

His Ser Ser Gly Ala Ala Phe Leu Ser Val Lys Lys Gln Phe Glu Glu
                100                 105                 110

Leu Thr Leu Ser Glu Phe Leu Lys Leu Asp Arg Glu Arg Ala Lys Asn
            115                 120                 125

Lys Ile Ala Lys Glu Thr Asn Asn Lys Lys Lys Glu Phe Glu Glu Thr
        130                 135                 140

Ala Lys Lys Val Arg Cys Ala Ile Glu Gln Leu Ala Ala Met Asp
145                 150                 155
```

<210> SEQ ID NO 3
<211> LENGTH: 696
<212> TYPE: DNA
<213> ORGANISM: Artificial Sequence
<220> FEATURE:
<223> OTHER INFORMATION: Synthetic Consensus Survivin isoform 1 +
      isoform 3 truncated DNA Coding Sequence pGX1429

<400> SEQUENCE: 3

```
atggattgga catggattct gttcctggtg gcagcagcaa ccagggtgca ctctggagca      60
ccaacactgc cccctgcatg gcagctgttt ctgaaggacc accggatcag caccttcaag     120
aactggcctt ttctggaggg ctgcgcctgt gccccagaga aatggcagag gcaggcttc     180 atccactgcc cagccgagaa tgagcctgat ctggcccagt gcttcttttg ttttaaggag    240
ctggagggct gggagcctga cgatgaccca atcgaggagc acaagaagca cagctccgga    300
gcagccttcc tgagcgtgaa gaagcagttt gaggagctga cactgtccga gttcctgaag    360
ctggataggg agcgcgccaa gaacaagatc gccaaggaga ccaacaacaa gaagaaggag    420
tttgaggaga cagccaagaa ggtgcggtgt gcaatcgagc agctggcagc aatggacagg    480
ggaagaaagc ggagatccat gcagaggaag cctaccatca ggcgcaagaa tctgcgcaag    540
ctgcggagaa agtgcgccgt gccatctagc tcctggctgc cctggacaga ggcctctggc    600
tggagctgtc tggtgcccga gtggctgcac cacttccagg gactgtttcc tggagccacc    660
tccctgccag tgggaccact ggccatgtct tgataa                               696
```

<210> SEQ ID NO 4
<211> LENGTH: 210
<212> TYPE: PRT
<213> ORGANISM: Artificial Sequence
<220> FEATURE:
<223> OTHER INFORMATION: Synthetic Consensus Survivin isoform 1 +
      isoform 3 truncated Protein Coding Sequence pGX1429

<400> SEQUENCE: 4

Met Asp Trp Thr Trp Ile Leu Phe Leu Val Ala Ala Thr Arg Val
1               5                   10                  15

His Ser Gly Ala Pro Thr Leu Pro Pro Ala Trp Gln Leu Phe Leu Lys
                20                  25                  30

Asp His Arg Ile Ser Thr Phe Lys Asn Trp Pro Phe Leu Glu Gly Cys
            35                  40                  45

Ala Cys Ala Pro Glu Arg Met Ala Glu Ala Gly Phe Ile His Cys Pro
        50                  55                  60

Ala Glu Asn Glu Pro Asp Leu Ala Gln Cys Phe Phe Cys Phe Lys Glu
65                  70                  75                  80

Leu Glu Gly Trp Glu Pro Asp Asp Pro Ile Glu Glu His Lys Lys
                85                  90                  95

His Ser Ser Gly Ala Ala Phe Leu Ser Val Lys Lys Gln Phe Glu Glu
                100                 105                 110

Leu Thr Leu Ser Glu Phe Leu Lys Leu Asp Arg Glu Arg Ala Lys Asn
            115                 120                 125

Lys Ile Ala Lys Glu Thr Asn Asn Lys Lys Glu Phe Glu Glu Thr
        130                 135                 140

Ala Lys Lys Val Arg Cys Ala Ile Glu Gln Leu Ala Ala Met Asp Arg
145                 150                 155                 160

Gly Arg Lys Arg Arg Ser Met Gln Arg Lys Pro Thr Ile Arg Arg Lys
                165                 170                 175

Asn Leu Arg Lys Leu Arg Arg Lys Cys Ala Val Pro Ser Ser Ser Trp
            180                 185                 190

Leu Pro Trp Thr Glu Ala Ser Gly Trp Ser Cys Leu Val Pro Glu Trp
        195                 200                 205

Leu His
    210

<210> SEQ ID NO 5
<211> LENGTH: 19
<212> TYPE: PRT
<213> ORGANISM: Artificial Sequence
<220> FEATURE:
<223> OTHER INFORMATION: matrix pools 1, 2, 3, 4, and 7

<400> SEQUENCE: 5

Leu Pro Pro Ala Trp Gln Leu Phe Leu Lys Asp His Arg Ile Ser Thr
1               5                   10                  15

Phe Lys Asn

<210> SEQ ID NO 6
<211> LENGTH: 19
<212> TYPE: PRT
<213> ORGANISM: Artificial Sequence
<220> FEATURE:
<223> OTHER INFORMATION: matrix pools 1, 2, 3, 4 and 11

<400> SEQUENCE: 6

Leu Lys Leu Asp Arg Glu Arg Ala Lys Asn Lys Ile Ala Lys Glu Thr

Asn Asn Lys

<210> SEQ ID NO 7
<211> LENGTH: 11
<212> TYPE: PRT
<213> ORGANISM: Artificial Sequence
<220> FEATURE:
<223> OTHER INFORMATION: matrix pools 3, 4 and 7

<400> SEQUENCE: 7

Glu Trp Leu His His Phe Gln Gly Leu Phe Pro
1               5                   10

<210> SEQ ID NO 8
<211> LENGTH: 232
<212> TYPE: PRT
<213> ORGANISM: Artificial Sequence
<220> FEATURE:
<223> OTHER INFORMATION: Synthetic Consensus Survivin isoform 1 +
      isoform 3 truncated Protein Coding Sequence pGX1429 Full Length

<400> SEQUENCE: 8

Met Asp Trp Thr Trp Ile Leu Phe Leu Val Ala Ala Thr Arg Val
1               5                   10                  15

His Ser Gly Ala Pro Thr Leu Pro Pro Ala Trp Gln Leu Phe Leu Lys
            20                  25                  30

Asp His Arg Ile Ser Thr Phe Lys Asn Trp Pro Phe Leu Glu Gly Cys
        35                  40                  45

Ala Cys Ala Pro Glu Arg Met Ala Glu Ala Gly Phe Ile His Cys Pro
    50                  55                  60

Ala Glu Asn Glu Pro Asp Leu Ala Gln Cys Phe Phe Cys Phe Lys Glu
65                  70                  75                  80

Leu Glu Gly Trp Glu Pro Asp Asp Pro Ile Glu Glu His Lys Lys
                85                  90                  95

His Ser Ser Gly Ala Ala Phe Leu Ser Val Lys Lys Gln Phe Glu Glu
            100                 105                 110

Leu Thr Leu Ser Glu Phe Leu Lys Leu Asp Arg Glu Arg Ala Lys Asn
        115                 120                 125

Lys Ile Ala Lys Glu Thr Asn Asn Lys Lys Glu Phe Glu Glu Thr
    130                 135                 140

Ala Lys Lys Val Arg Cys Ala Ile Glu Gln Leu Ala Ala Met Asp Arg
145                 150                 155                 160

Gly Arg Lys Arg Arg Ser Met Gln Arg Lys Pro Thr Ile Arg Arg Lys
                165                 170                 175

Asn Leu Arg Lys Leu Arg Arg Lys Cys Ala Val Pro Ser Ser Ser Trp
            180                 185                 190

Leu Pro Trp Thr Glu Ala Ser Gly Trp Ser Cys Leu Val Pro Glu Trp
        195                 200                 205

Leu His His Phe Gln Gly Leu Phe Pro Gly Ala Thr Ser Leu Pro Val
    210                 215                 220

Gly Pro Leu Ala Met Glu Thr Ser
225                 230

<210> SEQ ID NO 9
<211> LENGTH: 369
<212> TYPE: DNA
<213> ORGANISM: Artificial Sequence
<220> FEATURE:

<223> OTHER INFORMATION: Synthetic Consensus Survivin isoform 1 DNA
      Coding Sequence pGX1428

<400> SEQUENCE: 9

```
ggagccccca cactgccccc tgcctggcag ctgtttctga aggaccacag gatctctaca    60
ttcaagaact ggccctttct ggagggatgc gcatgtgcac ctgagaggat ggcagaggca   120
ggcttcatcc actgccctgc cgagaatgag ccagatctgg cccagtgctt cttttgtttt   180
aaggagctgg agggctggga gccagacgat gaccccatcg aggagcacaa gaagcacagc   240
tccggcgccg ccttcctgtc tgtgaagaag cagtttgagg agctgaccct gagcgagttc   300
ctgaagctgg atcgggagag agccaagaac aagatcgcca aggagaccaa caacaagaag   360
aaggagttt                                                          369
```

<210> SEQ ID NO 10
<211> LENGTH: 582
<212> TYPE: DNA
<213> ORGANISM: Artificial Sequence
<220> FEATURE:
<223> OTHER INFORMATION: Synthetic Consensus Survivin isoform 1 +
      isoform 3 truncated DNA Coding Sequence pGX1429

<400> SEQUENCE: 10

```
ggagcaccaa cactgccccc tgcatggcag ctgtttctga aggaccaccg gatcagcacc    60
ttcaagaact ggccttttct ggagggctgc gcctgtgccc cagagagaat ggcagaggca   120
ggcttcatcc actgcccagc cgagaatgag cctgatctgg cccagtgctt cttttgtttt   180
aaggagctgg agggctggga gcctgacgat gacccaatcg aggagcacaa gaagcacagc   240
tccggagcag ccttcctgag cgtgaagaag cagtttgagg agctgacact gtccgagttc   300
ctgaagctgg atagggagcg cgccaagaac aagatcgcca aggagaccaa caacaagaag   360
aaggagtttg aggagacagc caagaaggtg cggtgtgcaa tcgagcagct ggcagcaatg   420
gacaggggaa gaaagcggag atccatgcag aggaagccta ccatcaggcg caagaatctg   480
cgcaagctgc ggagaaagtg cgccgtgcca tctagctcct ggctgccctg gacagaggcc   540
tctggctgga gctgtctggt gcccgagtgg ctgcaccact tc                     582
```

<210> SEQ ID NO 11
<211> LENGTH: 141
<212> TYPE: PRT
<213> ORGANISM: Artificial Sequence
<220> FEATURE:
<223> OTHER INFORMATION: Synthetic Consensus Survivin isoform 1 Protein
      Coding Sequence pGX1428

<400> SEQUENCE: 11

```
Gly Ala Pro Thr Leu Pro Pro Ala Trp Gln Leu Phe Leu Lys Asp His
1               5                   10                  15

Arg Ile Ser Thr Phe Lys Asn Trp Pro Phe Leu Glu Gly Cys Ala Cys
                20                  25                  30

Ala Pro Glu Arg Met Ala Glu Ala Gly Phe Ile His Cys Pro Ala Glu
            35                  40                  45

Asn Glu Pro Asp Leu Ala Gln Cys Phe Phe Cys Phe Lys Glu Leu Glu
        50                  55                  60

Gly Trp Glu Pro Asp Asp Asp Pro Ile Glu Glu His Lys Lys His Ser
65                  70                  75                  80

Ser Gly Ala Ala Phe Leu Ser Val Lys Lys Gln Phe Glu Glu Leu Thr
                85                  90                  95
```

```
Leu Ser Glu Phe Leu Lys Leu Asp Arg Glu Arg Ala Lys Asn Lys Ile
            100                 105                 110

Ala Lys Glu Thr Asn Asn Lys Lys Glu Phe Glu Glu Thr Ala Lys
        115                 120                 125

Lys Val Arg Cys Ala Ile Glu Gln Leu Ala Ala Met Asp
    130                 135                 140

<210> SEQ ID NO 12
<211> LENGTH: 192
<212> TYPE: PRT
<213> ORGANISM: Artificial Sequence
<220> FEATURE:
<223> OTHER INFORMATION: Synthetic Consensus Survivin isoform 1 +
      isoform 3 truncated Protein Coding Sequence pGX1429

<400> SEQUENCE: 12

Gly Ala Pro Thr Leu Pro Pro Ala Trp Gln Leu Phe Leu Lys Asp His
1               5                   10                  15

Arg Ile Ser Thr Phe Lys Asn Trp Pro Phe Leu Glu Gly Cys Ala Cys
            20                  25                  30

Ala Pro Glu Arg Met Ala Glu Ala Gly Phe Ile His Cys Pro Ala Glu
        35                  40                  45

Asn Glu Pro Asp Leu Ala Gln Cys Phe Phe Cys Phe Lys Glu Leu Glu
    50                  55                  60

Gly Trp Glu Pro Asp Asp Asp Pro Ile Glu Glu His Lys Lys His Ser
65                  70                  75                  80

Ser Gly Ala Ala Phe Leu Ser Val Lys Lys Gln Phe Glu Glu Leu Thr
                85                  90                  95

Leu Ser Glu Phe Leu Lys Leu Asp Arg Glu Arg Ala Lys Asn Lys Ile
            100                 105                 110

Ala Lys Glu Thr Asn Asn Lys Lys Glu Phe Glu Glu Thr Ala Lys
        115                 120                 125

Lys Val Arg Cys Ala Ile Glu Gln Leu Ala Ala Met Asp Arg Gly Arg
    130                 135                 140

Lys Arg Arg Ser Met Gln Arg Lys Pro Thr Ile Arg Arg Lys Asn Leu
145                 150                 155                 160

Arg Lys Leu Arg Arg Lys Cys Ala Val Pro Ser Ser Ser Trp Leu Pro
                165                 170                 175

Trp Thr Glu Ala Ser Gly Trp Ser Cys Leu Val Pro Trp Leu His
            180                 185                 190

<210> SEQ ID NO 13
<211> LENGTH: 214
<212> TYPE: PRT
<213> ORGANISM: Artificial Sequence
<220> FEATURE:
<223> OTHER INFORMATION: Synthetic Consensus Survivin isoform 1 +
      isoform 3 truncated Protein Coding Sequence pGX1429 Full Length

<400> SEQUENCE: 13

Gly Ala Pro Thr Leu Pro Pro Ala Trp Gln Leu Phe Leu Lys Asp His
1               5                   10                  15

Arg Ile Ser Thr Phe Lys Asn Trp Pro Phe Leu Glu Gly Cys Ala Cys
            20                  25                  30

Ala Pro Glu Arg Met Ala Glu Ala Gly Phe Ile His Cys Pro Ala Glu
        35                  40                  45

Asn Glu Pro Asp Leu Ala Gln Cys Phe Phe Cys Phe Lys Glu Leu Glu
    50                  55                  60
```

-continued

```
Gly Trp Glu Pro Asp Asp Pro Ile Glu His Lys Lys His Ser
 65                  70              75              80

Ser Gly Ala Ala Phe Leu Ser Val Lys Lys Gln Phe Glu Glu Leu Thr
             85                  90                  95

Leu Ser Glu Phe Leu Lys Leu Asp Arg Glu Arg Ala Lys Asn Lys Ile
            100                 105                 110

Ala Lys Glu Thr Asn Asn Lys Lys Lys Glu Phe Glu Glu Thr Ala Lys
        115                 120                 125

Lys Val Arg Cys Ala Ile Glu Gln Leu Ala Ala Met Asp Arg Gly Arg
        130                 135                 140

Lys Arg Arg Ser Met Gln Arg Lys Pro Thr Ile Arg Arg Lys Asn Leu
145                 150                 155                 160

Arg Lys Leu Arg Arg Lys Cys Ala Val Pro Ser Ser Ser Trp Leu Pro
            165                 170                 175

Trp Thr Glu Ala Ser Gly Trp Ser Cys Leu Val Pro Glu Trp Leu His
            180                 185                 190

His Phe Gln Gly Leu Phe Pro Gly Ala Thr Ser Leu Pro Val Gly Pro
        195                 200                 205

Leu Ala Met Glu Thr Ser
        210
```

CANCER VACCINES TARGETING SURVIVIN AND USES THEREOF

CROSS-REFERENCE TO RELATED APPLICATIONS

This application claims priority to and the benefit of U.S. Provisional Patent Application No. 62/598,267, filed Dec. 13, 2017, the disclosure of which is incorporated herein by reference in its entirety.

SEQUENCE LISTING

This application contains a Sequence Listing which has been submitted electronically in ASCII format and is hereby incorporated by reference in its entirety. Said ASCII copy, created Feb. 7, 2023, is named 104409_000454_Sequence_listing_ST25.txt and is 15,799 bytes in size.

TECHNICAL FIELD

The present invention relates to Survivin antigens and nucleic acid molecules encoding the same. The present invention also relates to vaccines including such Survivin antigens and/or nucleic acid molecules. The present invention further relates to methods of using the vaccines for inducing immune responses and preventing and/or treating subjects having cancer cells and/or tumors that express Survivin.

BACKGROUND

Cancer is among the leading causes of death worldwide. In the United States, cancer is the second most common cause of death, accounting for nearly 1 of every 4 deaths. Cancer arises from a single cell that has transformed from a normal cell into a cancerous cell. Such a transformation is often a multistage process, progressing from a pre-cancerous lesion to malignant tumors. Multiple factors contribute to this progression, including aging, genetic contributions, and exposure to external agents such as physical carcinogens (e.g., ultraviolet and ionizing radiation), chemical carcinogens (e.g., asbestos, components of tobacco smoke, etc.), and biological carcinogens (e.g., certain viruses, bacteria, and parasites).

Prevention, diagnosis, and treatment of cancer may take many different forms. Prevention may include screening for pre-disposing factors (e.g., specific genetic variants), altering behavior (e.g., smoking, diet, and amount of physical activity), and vaccination against viruses (e.g., human papilloma virus hepatitis B virus). Treatment may include chemotherapy, radiation therapy, and surgical removal of a tumor or cancerous tissue. Despite the availability of numerous prevention and treatment methods, such methods often meet with limited success in effectively preventing and/or treating the cancer.

Survivin, also known as baculoviral inhibitor of apoptosis repeat-containing 5 (BIRC5), is an apoptosis inhibitor that blocks caspase function and thereby prevents programmed cell death. In addition to its role in apoptosis, Survivin unequivocally has an essential, evolutionarily conserved role in mitosis. (Li, F. et al. Control of apoptosis and mitotic spindle checkpoint by Survivin. Nature 396, 580-584 (1998).) Overexpression of Survivin is associated with tumor cell proliferation, progression, angiogenesis, therapeutic resistance and poor prognosis. In healthy cells and tissues, Survivin expression is either absent, or present at low levels. However, Survivin is a member of the inhibitor of apoptosis protein (IAP) family, and IAP genes are highly expressed in different cancer cells and primary tumor biopsies. Among the IAPs, Survivin exhibits the most dramatic overexpression in tumors and fetal tissues. In multiple studies of ovarian carcinoma, the number of patient samples testing positive for Survivin expression ranged from 74 to 92%. (See Cohen, C., Lohmann, C. M., Cotsonis, G., Lawson, D. & Santoianni, R. Survivin expression in ovarian carcinoma: correlation with apoptotic markers and prognosis. Modern pathology: an official journal of the United States and Canadian Academy of Pathology, Inc 16, 574-583 (2003); Felisiak-Golabek, A. et al. Nuclear Survivin expression is a positive prognostic factor in taxane-platinum-treated ovarian cancer patients. Journal of ovarian research 4, 20 (2011).) Survivin's contribution to oncogenesis, combined with its restricted pattern of expression and overexpression in various tumors, make it an attractive target for cancer immunotherapy.

Survivin is the smallest member of the IAP family. It is a 16.3 kD protein consisting of 142 amino acids and is characterized by the presence of a single BIR repeat. It also lacks a carboxyl terminal RING finger domain in its protein structure. (Chen, X., Duan, N., Zhang, C. & Zhang, W. Survivin and Tumorigenesis: Molecular Mechanisms and Therapeutic Strategies. Journal of Cancer 7, 314-323 (2016).) Several Survivin isoforms have been identified, and Survivin isoform 1 is the dominant transcript. Survivin is expressed during fetal development, but is not expressed in fully differentiated tissues. It is, however, highly expressed in many cancer cells. Thus, Survivin is a potential target antigen for the treatment of cancers.

Vaccines for the treatment and prevention of cancer, and epithelial ovarian cancer (EOC) in particular, are of interest. However, existing vaccines targeting tumor cell antigens are limited by poor antigen expression in vivo. Accordingly, a need remains in the art for safe and effective vaccines and methods of their use for preventing and/or treating cancer and reducing mortality in subjects suffering from cancer.

SUMMARY OF THE INVENTION

Provided herein are:

Nucleic acid molecules comprising one or more nucleic acid sequences selected from the group consisting of: (a) a nucleic acid sequence that encodes SEQ ID NO: 11 (amino acids 19-159 of SEQ ID NO:2); (b) a nucleic acid sequence that encodes SEQ ID NO: 12 (amino acids 19-210 of SEQ ID NO:4); (c) a nucleic acid sequence that encodes SEQ ID NO: 13 (amino acids 19-232 of SEQ ID NO:8); (d) a nucleic acid sequence that encodes a fragment comprising at least 90% of an entire length of amino acids 19-159 of SEQ ID NO:2; (e) a nucleic acid sequence that encodes a fragment comprising at least 90% of an entire length of amino acids 19-210 of SEQ ID NO:4; (f) a nucleic acid sequence that encodes a fragment comprising at least 90% of an entire length of amino acids 19-232 of SEQ ID NO:8; (g) a nucleic acid sequence that encodes a protein that is at least 95% identical to amino acids 19-159 of SEQ ID NO:2; (h) a nucleic acid sequence that encodes a protein that is at least 95% identical to amino acids 19-210 of SEQ ID NO:4; (i) a nucleic acid sequence that encodes a protein that is at least 95% identical to amino acids 19-232 of SEQ ID NO:8; (j) a nucleic acid sequence that encodes a fragment comprising at least 90% of an entire length of a protein that is at least 95% identical to amino acids 19-159 of SEQ ID NO:2; (k) a nucleic acid sequence that encodes a fragment comprising at least 90% of an entire length of a protein that is at least 95% identical to amino acids 19-210 of SEQ ID NO:4; and (1) a nucleic acid sequence that encodes a fragment comprising at least 90% of an entire length of a protein that is at least 95% identical to amino acids 19-232 of SEQ ID NO:8.

Nucleic acid molecules comprising one or more nucleic acid sequences selected from the group consisting of: (a) SEQ ID NO: 9 (nucleotides 55-423 of SEQ ID NO:1); (b) SEQ ID NO: 10 (nucleotides 55-636 of SEQ ID NO:3); (c) a fragment comprising at least 90% of an entire length of nucleotides 55-423 of SEQ ID NO:1; (d) a fragment comprising at least 90% of an entire length of nucleotides 55-636 of SEQ ID NO:3; (e) a fragment that is at least 95% identical to nucleotides 55-423 of SEQ ID NO:1; (f) a fragment that is at least 95% identical to nucleotides 55-636 of SEQ ID NO:3; (g) a fragment comprising at least 90% of a nucleic acid sequence that is at least 95% identical to nucleotides 55-423 of SEQ ID NO:1; and (h) a fragment comprising at least 90% of a nucleic acid sequence that is at least 95% identical to nucleotides 55-636 of SEQ ID NO:3.

Nucleic acid molecules comprising one or more nucleic acid sequences selected from the group consisting of: (a) a nucleic acid sequence that encodes SEQ ID NO:2; (b) a nucleic acid sequence that encodes SEQ ID NO:4; (c) a nucleic acid sequence that encodes SEQ ID NO:8; (d) a nucleic acid sequence that encodes a fragment comprising at least 90% of an entire length of SEQ ID NO:2; (e) a nucleic acid sequence that encodes a fragment comprising at least 90% of an entire length of SEQ ID NO:4; (f) a nucleic acid sequence that encodes a fragment comprising at least 90% of an entire length of SEQ ID NO:8; (g) a nucleic acid sequence that encodes a protein that is at least 95% identical to SEQ ID NO:2; (h) a nucleic acid sequence that encodes a protein that is at least 95% identical to SEQ ID NO:4; (i) a nucleic acid sequence that encodes a protein that is at least 95% identical to SEQ ID NO:8; (j) a nucleic acid sequence that encodes a fragment comprising at least 90% of an entire length of a protein that is at least 95% identical to SEQ ID NO:2; (k) a nucleic acid sequence that encodes a fragment comprising at least 90% of an entire length of a protein that is at least 95% identical to SEQ ID NO:4; and (1) a nucleic acid sequence that encodes a fragment comprising at least 90% of an entire length of a protein that is at least 95% identical to SEQ ID NO:8.

Nucleic acid molecules comprising one or more nucleic acid sequences selected from the group consisting of: (a) SEQ ID NO:1; (b) SEQ ID NO:3; (c) a fragment comprising at least 90% of an entire length of SEQ ID NO:1; (d) a fragment comprising at least 90% of an entire length of SEQ ID NO:3; (e) a fragment that is at least 95% identical to SEQ ID NO:1; (f) a fragment that is at least 95% identical to SEQ ID NO:3; (g) a fragment comprising at least 90% of an entire length of a nucleic acid sequence that is at least 95% identical to SEQ ID NO:1; and (h) a fragment comprising at least 90% of an entire length of a nucleic acid sequence that is at least 95% identical to SEQ ID NO:3.

Nucleic acid molecules comprising the nucleic acid sequence set forth in SEQ ID NO:1.

Nucleic acid molecules comprising the nucleic acid sequence set forth in SEQ ID NO:3.

Nucleic acid molecules as described herein for use as a medicament.

Nucleic acid molecules as described herein for use as a medicament in the treatment of cancer.

Nucleic acid molecules as described herein for use in the preparation of a medicament.

Nucleic acid molecules as described herein for use in the preparation of a medicament for the treatment of cancer.

Vectors comprising the nucleic acid molecule as described herein.

Vectors comprising a plasmid or a viral vector.

Compositions comprising one or more nucleic acid molecules as described herein.

Compositions as described herein comprising a pharmaceutically acceptable carrier.

Compositions as described herein comprising one or more vectors as described herein.

Proteins comprising the amino acid sequence selected from the group consisting of: (a) amino acids 19-159 of SEQ ID NO:2; (b) amino acids 19-210 of SEQ ID NO:4; (c) amino acids 19-232 of SEQ ID NO:8; (d) a fragment comprising at least 90% of an entire length of amino acids 19-159 of SEQ ID NO:2; (e) a fragment comprising at least 90% of an entire length of amino acids 19-210 of SEQ ID NO 4; (f) a fragment comprising at least 90% of an entire length of amino acids 19-232 of SEQ ID NO:8; (g) an amino acid sequence that is at least 95% identical to amino acids 19-159 of SEQ ID NO:2; (h) an amino acid sequence that is at least 95% identical to amino acids 19-210 of SEQ ID NO:4; (i) an amino acid sequence that is at least 95% identical to amino acids 19-232 of SEQ ID NO:8; (j) a fragment comprising at least 90% of an entire length of an amino acid sequence that is at least 95% identical to amino acids 19-159 of SEQ ID NO:2; (k) a fragment comprising at least 90% of an entire length of an amino acid sequence that is at least 95% identical to amino acids 19-210 of SEQ ID NO:4; and (1) a fragment comprising at least 90% of an entire length of an amino acid sequence that is at least 95% identical to amino acids 19-232 of SEQ ID NO:8.

Proteins comprising the amino acid sequence selected from the group consisting of: (a) SEQ ID NO:2; (b) SEQ ID NO:4; (c) SEQ ID NO:8; (d) a fragment comprising at least 90% of an entire length of SEQ ID NO:2; (e) a fragment comprising at least 90% of an entire length of SEQ ID NO:4; (f) a fragment comprising at least 90% of an entire length of SEQ ID NO:8; (g) an amino acid sequence that is at least 95% identical to SEQ ID NO:2; (h) an amino acid sequence that is at least 95% identical to SEQ ID NO:4; (i) an amino acid sequence that is at least 95% identical to SEQ ID NO:8; (j) a fragment comprising at least 90% of an entire length of an amino acid sequence that is at least 95% identical to SEQ ID NO:2; (k) a fragment comprising at least 90% of an entire length of an amino acid sequence that is at least 95% identical to SEQ ID NO:4; and (1) a fragment comprising at least 90% of an entire length of an amino acid sequence that is at least 95% identical to SEQ ID NO:8.

Proteins comprising the amino acid sequence set forth in SEQ ID NO:2.

Proteins comprising the amino acid sequence set forth in SEQ ID NO:4.

Proteins comprising the amino acid sequence set forth in SEQ ID NO:8.

Vaccines comprising the nucleic acid molecules as described herein.

Vaccines comprising the vector as described herein.

Vaccines as described herein, further comprising a pharmaceutically acceptable excipient.

Vaccines as described herein, further comprising an adjuvant.

Vaccines as described herein, wherein the adjuvant is IL-12, IL-15, IL-28, or RANTES.

Methods of treating a subject with a Survivin-expressing cancerous cell comprising administering a therapeutically effective amount of a vaccine as described herein.

Methods as described herein, wherein administration includes an electroporation step.

Methods as described herein, wherein administration occurs at one or more sites on the subject.

Methods of vaccinating a subject against a Survivin-expressing cancerous cell comprising administering an amount of a vaccine as described herein effective to induce a humoral or cellular immune response.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In the drawings:

FIGS. 7A to 7H show immunogenicity of synthetic consensus Survivin antigen 1 and synthetic consensus Survivin antigen 1T3. Female CB6F1 were immunized 3 times, 3 weeks apart with the indicated dose amounts of Survivin 1 (pGX1428) (FIGS. 7A-7D), Survivin 1T3 pGX1429 (E-H) (n=8/group), or pGX0001 (empty vector) (n=4). FIG. 7A: Survivin 1 specific IFNγ responses by ELISpot at indicated dose amounts of pGX1428. FIG. 7B: Survivin 1 specific CD4+ T cell responses. FIG. 7C. Survivin 1 specific CD8+ T cell responses. FIG. 7D: Survivin 1T3 specific IFNγ responses by ELISpot at indicated dose amounts of pGX1429. FIG. 7E: Survivin 1T3 specific CD4+ T cell responses. FIG. 7F: Survivin 1T3 specific CD8+ T cell responses. FIG. 7G: Cytokine profile of Survivin 1 specific CD4+ T cell and CD8+ T cell responses. FIG. 7H: Cytokine profile of Survivin 1T3 specific CD4+ T cell and CD8+ T cell responses.

FIG. 10A: Frequency of Survivin 1 specific CD4+CD107a+ T cells. FIG. 10B: Frequency of Survivin 1T3 specific CD4+CD107a+ T cells. FIG. 10C: Cytokine profile of CD4+CD107a+ T cells. FIG. 10D: Frequency of Survivin 1 specific CD8+CD107a+ T cells. FIG. 10E: Frequency of Survivin 1T3 specific CD8+CD107a+ T cells. FIG. 10F: Cytokine profile of CD4+ CD107a+ T cells.

FIGS. 11A to 11D show epitope mapping of Survivin IFN-gamma responses. Breadth of IFNγ responses induced by Survivin 1 and Survivin 1T3. FIG. 11A: Survivin 1 peptide pools after treatment with 50 μg of pGX1428, pGX1429 or pGX0001. FIG. 11B: Survivin T3 peptide pools after treatment with 50 μg of pGX1429 or pGX0001. Sequence comparison of pGX1428 and pGX1429 with position of matrix pools indicated in by dashed-line boxes. FIG. 11C: Sequence comparison of pGX1428 and pGX1429. Amino acids in red text indicate epitopes identified by matrix mapping. The underlined text represents sequence portions that are added to the synthetic consensus Survivin antigen: N-terminus indicates the IgELS and RGRKRRS furin cleavage site. FIG. 11D: Survivin 1 and Survivin T3 matrix design. Peptides that elicited a response are indicated by dashed-line boxes.

FIG. 15A shows Group 1 animal results; FIG. 15B shows Group 2 animal results; and FIG. 15C shows Group 3 animal results.

DETAILED DESCRIPTION OF THE INVENTION

Figure 1:
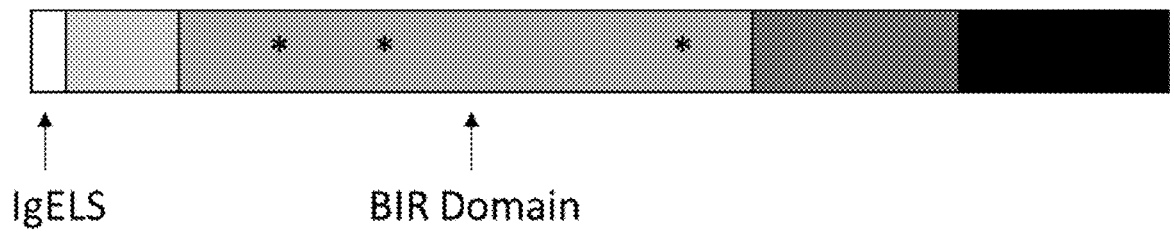
FIG. 1 shows a schematic representation of synthetic consensus Survivin antigen isoform 1. Asterisks denote mutations essential for abolishing anti-apoptotic activity.

The present invention relates to vaccines comprising a synthetic consensus Survivin antigen. Survivin is expressed in many tumors. Accordingly, the vaccine provides treatment for a cancer or cancer-based tumors expressing Survivin.

The synthetic consensus Survivin antigen can be a consensus Survivin antigen derived from the sequences of Survivin from different species or from different isoforms within a species, and thus, the synthetic consensus Survivin antigen is non-native. The consensus Survivin antigen can be further modified by introducing one or more mutations into the consensus sequence to generate a synthetic consensus sequence. The mutations can interrupt or modify particular functional domains of the native Survivin sequence, thereby disrupting or enhancing the structure or function of the functional domains. In some embodiments, additional sequences are added to the synthetic consensus Survivin antigen sequence to introduce new structures or functions. For example, the synthetic consensus Survivin antigen sequence may have a furin cleavage site. The synthetic consensus Survivin antigen sequence may include an additional localization signal to enhance extracellular transport of the ultimate protein product. The additional localization signal may be an IgELS or other cellular transport sequence The synthetic consensus Survivin antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-7) and/or tumor necrosis factor alpha (TNF-α) and/or interleukin 2 (IL-2). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumor associated macrophages, tumor associated fibroblasts, soluble factors produced by immune suppressor cells, CTLA-4, PD-1, MDSCs, MCP-1, and an immune checkpoint molecule.

The vaccine of the invention can provide any combination of particular cancer antigens for the particular prevention or treatment of the cancer of a subject that is in need of treatment.

One manner for designing the nucleic acid and its encoded amino acid sequence of the recombinant cancer antigen is by introducing mutations that change particular amino acids in the overall amino acid sequence of the native cancer antigen. The introduction of mutations does not alter the cancer antigen so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer antigen that has at least 85% and up to 99% amino acid sequence identity compared to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen has 95%, 96%, 97%, 98%, or 99% amino acid sequence identity compared to its corresponding native cancer antigen. The native cancer antigen is the antigen normally associated with the particular cancer or cancer tumor. Depending upon the cancer antigen, the consensus sequence of the cancer antigen can be across mammalian species or within subtypes of a species or across viral strains or serotypes. Some cancer antigens do not vary greatly from the wild type amino acid sequence of the cancer antigen. Some cancer antigens have nucleic acid/amino acid sequences that are so divergent across species, that a consensus sequence cannot be generated. In these instances, a recombinant cancer antigen that will break tolerance and generate an immune response is generated that has at least 85% and up to 99% amino acid sequence identity compared to its corresponding native cancer antigen; preferably at least 90% and up to 98% sequence identity; more preferably at least 93% and up to 98% sequence identity; or even more preferably at least 95% and up to 98% sequence identity. In some instances the recombinant cancer antigen has 95%, 96%, 97%, 98%, or 99% amino acid sequence identity compared to its corresponding native cancer antigen. The aforementioned approaches can be combined so that the final recombinant cancer antigen has a percent similarity to native cancer antigen amino acid sequence as discussed, above.

The vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses. Overall, designing the cancer antigens to be recognized by the immune system helps to overcome other forms of immune suppression by tumor cells, and these vaccines can be used in combination with suppression or inhibition therapies (such as anti-PD-1 and anti-PDL-1 antibody therapies) to further increase T-cell and/or B-cell responses.

The vaccine can increase tumor free survival by 30%, 31%, 32%, 33%, 34%, 35%, 36%, 37%, 38%, 39% 40%, 41%, 42%, 43%, 44%, and 45%. The vaccine can reduce tumor mass by 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, and 60% after immunization. The vaccine can prevent and block increases in monocyte chemoattractant protein 1 (MCP-1), a cytokine secreted by myeloid derived suppressor cells. The vaccine can increase tumor survival by 30%, 31%, 32%, 33%, 34%, 35%, 36%, 37%, 38%, 39%, 40%, 41%, 42%, 43%, 44%, 45%, 46%, 47%, 48%, 49%, 50%, 5%, %52%, 53%, 54%, 55%, 56%, 57%, 58%, 59%, and 60%.

The vaccine can increase a cellular immune response in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine. In some embodiments the vaccine can increase the cellular immune response in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the vaccine.

The vaccine can increase interferon gamma (IFN-7) levels in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-7 levels in a subject not administered the vaccine. In some embodiments the vaccine can increase IFN-7 levels in the subject administered the vaccine by about 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-7 levels in the subject not administered the vaccine.

As described in more detail below, the vaccine can further comprise one or more inhibitors of one or more immune checkpoint molecules (i.e., an immune checkpoint inhibitor). Immune checkpoint molecules are described below in more detail. The immune checkpoint inhibitor is any nucleic acid or protein that prevents the suppression of any component in the immune system such as NMC class presentation, T cell presentation and/or differentiation, B cell presentation and/or differentiation, any cytokine, chemokine or signaling for immune cell proliferation and/or differentiation. As also described below in more detail, the vaccine may be combined further with antibodies to checkpoint inhibitors such as PD-1 and PDL-1 to increase the stimulation of both the cellular and humoral immune responses. Using anti-PD-1 or anti-PDL-1 antibodies prevents PD-1 or PDL-1 from suppressing T-cell and/or B-cell responses.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For recitation of numeric ranges herein, each intervening value having the same degree of precision as the recited range minimum and maximum is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the vaccines described herein to enhance the immunogenicity of the antigen.

"Antibody" as used herein means an antibody of class IgG, IgM, IgA, IgD, or IgE, or fragment, or derivative thereof, including Fab, $F(ab')_2$, Fd, and single chain antibodies, diabodies, bispecific antibodies, bifunctional antibodies, and derivatives thereof. The antibody can be an antibody isolated from the serum sample of a mammal, a polyclonal antibody, an affinity purified antibody, or any mixture thereof which exhibits sufficient binding specificity to a desired epitope or a sequence derived therefrom.

"Antigen" refers to proteins having synthetic consensus Survivin antigen amino acid sequences including: (a) amino acids 19-159 of SEQ ID NO:2; (b) amino acids 19-210 of SEQ ID NO:4; (c) amino acids 19-232 of SEQ ID NO:8; (d) fragments comprising at least 90% of amino acids 19-159 of SEQ ID NO:2; (e) fragments comprising at least 90% of amino acids 19-210 of SEQ ID NO:4; (f) fragments comprising at least 90% of amino acids 19-232 of SEQ ID NO:8; (g) proteins that are at least 95% identical to amino acids 19-159 of SEQ ID NO:2; (h) proteins that are at least 95% identical to amino acids 19-210 of SEQ ID NO:4; (i) proteins that are at least 95% identical to amino acids 19-232 of SEQ ID NO:8; (j) fragments comprising at least 90% of a protein that is at least 95% identical to amino acids 19-159 of SEQ ID NO:2; (k) fragments comprising at least 90% of a protein that is at least 95% identical to amino acids 19-210 of SEQ ID NO:4; and (1) fragments comprising at least 90% of a protein that is at least 95% identical to amino acids 19-232 of SEQ ID NO:8. "Antigen" also refers to proteins having synthetic consensus Survivin antigen amino acid sequences including (a) SEQ ID NO:2; (b) SEQ ID NO:4; (c) SEQ ID NO:8; (d) fragments comprising at least 90% of an entire length of SEQ ID NO:2; (e) fragments comprising at least 90% of an entire length of SEQ ID NO:4; (f) fragments comprising at least 90% of an entire length of SEQ ID NO:8; (g) proteins that are at least 95% identical to SEQ ID NO:2; (h) proteins that are at least 95% identical to SEQ ID NO:4; (i) proteins that are at least 95% identical to SEQ ID NO:8; (j) fragments comprising at least 90% of an entire length of a protein that is at least 95% identical to SEQ ID NO:2; (k) fragments comprising at least 90% of an entire length of a protein that is at least 95% identical to SEQ ID NO:4; and (1) fragments comprising at least 90% of an entire length of a protein that is at least 95% identical to SEQ ID NO:8. Antigens may optionally include signal peptides such as those from other proteins.

"Coding sequence" or "encoding nucleic acid" as used herein means the nucleic acids (RNA or DNA molecule) that comprise a nucleotide sequence encoding a protein. The coding sequence can further include initiation and termination signals operably linked to regulatory elements including a promoter and polyadenylation signal capable of directing expression in the cells of a subject or mammal to which the nucleic acid is administered.

"Complement" or "complementary" as used herein with regard to a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms or from different isoforms within an organism. Nucleic acid sequences that encode a consensus polypeptide sequence can be prepared.

"Constant current" as used herein describes a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below, excluding an heterologous signal peptide added. The fragment may comprise at least 95%, at least 96%, at least 97%, at least 98%, or at least 99% of one or more of the nucleic acid sequences set forth below and additionally optionally comprise sequence encoding a heterologous signal peptide, which need not be included when calculating percent identity. Fragments may further comprise coding sequences for a signal peptide such as an immunoglobulin signal peptide, for example an IgE or IgG signal peptide. The coding sequence encoding an N terminal methionine and/or signal peptide may be linked to a fragment of coding sequence.

In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, or at least 650 nucleotides or more of at least one of the nucleic acid sequences set forth below.

"Fragment" or "immunogenic fragment" with respect to polypeptide sequences means a polypeptide capable of eliciting an immune response in a mammal that cross-reacts with an antigen disclosed herein. The fragments can be polypeptide fragments selected from at least one of the various amino acids sequences below. Fragments of consensus proteins can comprise at least 10%, at least 20%, at least 30%, at least 40%, at least 50%, at least 60%, at least 70%, at least 80%, at least 90% or at least 95% of a consensus protein, excluding any heterologous signal peptide added. The fragment may comprise at least 95%, at least 96%, at least 97%, at least 98%, or at least 99% of one or more of the amino sequences set forth below and additionally optionally comprise a heterologous signal peptide, which need not be included when calculating percent identity. Fragments may further comprise a signal peptide such as an immunoglobulin signal peptide, for example an IgE or IgG signal peptide.

In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 200 amino acids or more, or at least 220 amino acids or more of a protein sequence disclosed herein.

As used herein, the term "genetic construct" refers to the DNA or RNA molecules that comprise a nucleotide sequence that encodes a protein. The coding sequence includes initiation and termination signals operably linked to regulatory elements including a promoter and polyadenylation signal capable of directing expression in the cells of the subject to whom the nucleic acid molecule is administered. As used herein, the term "expressible form" refers to a gene construct that contain the necessary regulatory elements operably linked to a coding sequence that encodes a protein such that, when present in cell of a subject, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally derived molecule that is capable of conferring, activating, or enhancing expression of a nucleic acid in a cell. A promoter can comprise one or more specific transcriptional regulatory sequences to further enhance expression and/or to alter the spatial expression and/or temporal expression of a nucleic acid in a cell. A promoter can also comprise distal enhancer or repressor elements, which can be located as much as several thousand base pairs from the start site of transcription. A promoter can be derived from sources including viral, bacterial, fungal, plant, insect, and animal. A promoter can regulate the expression of a gene component constitutively or differentially with respect to cell, tissue, or organ in which expression occurs, or with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a human, chimpanzee, dog, cat, horse, cow, mouse, or rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treat," "treatment," or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" as used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

"Variant" as used herein with respect to a peptide or polypeptide means a peptide or polypeptide that differs in amino acid sequence by the insertion, deletion, or conservative substitution of amino acids, but retains at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of 2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%0, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

Vaccines

Provided herein are vaccines comprising a synthetic consensus Survivin antigen as disclosed herein, a nucleic acid molecule encoding an antigen, a nucleic acid molecule encoding a fragment of an antigen, a nucleic acid molecule encoding a variant of an antigen, or nucleic acid molecules encoding combinations thereof. The vaccines can be capable of generating in a subject an immune response against the antigen. The immune response can be a therapeutic or prophylactic immune response. The vaccines may comprise a vector or a plurality of vectors as described in more detail below.

In some embodiments, the vaccine comprises a nucleic acid molecule. In some embodiments, the nucleic acid molecule encodes a synthetic consensus Survivin antigen. In some embodiments, the nucleic acid molecule comprises a nucleic acid sequence that encodes SEQ ID NO: 3; a nucleic acid sequence that encodes a fragment comprising at least 90% of the length of SEQ ID NO 3; a nucleic acid sequence that encodes a protein that is at least 95% identical to SEQ ID NO: 3; or a nucleic acid sequence that encodes a fragment comprising at least 90% of an entire length of a protein that is at least 95% identical to SEQ ID NO: 3. In some embodiments, the nucleic acid molecule comprises SEQ ID NO: 1; a fragment comprising at least 90% of the entire length of SEQ ID NO: 1; a fragment that is at least 95% identical to SEQ ID NO: 1; or a fragment comprising at least 90% of the entire length of a nucleic acid sequence that is at least 95% identical to SEQ ID NO: 1.

In some embodiments, the nucleic acid molecule comprises a nucleic acid sequence that encodes SEQ ID NO: 4;

a nucleic acid sequence that encodes a fragment comprising at least 90% of the length of SEQ ID NO 4; a nucleic acid sequence that encodes a protein that is at least 95% identical to SEQ ID NO: 4; or a nucleic acid sequence that encodes a fragment comprising at least 90% of an entire length of a protein that is at least 95% identical to SEQ ID NO: 4. In some embodiments, the nucleic acid molecule comprises SEQ ID NO: 2; a fragment comprising at least 90% of the entire length of SEQ ID NO: 2; a fragment that is at least 95% identical to SEQ ID NO: 2; or a fragment comprising at least 90% of the entire length of a nucleic acid sequence that is at least 95% identical to SEQ ID NO: 2.

In some embodiments, the vaccine comprises a synthetic consensus Survivin antigen, wherein the antigen comprises SEQ ID NO: 3; a fragment comprising at least 90% of the length of SEQ ID NO 3; an amino acid sequence that is at least 95% identical to SEQ ID NO: 3; or a fragment comprising at least 90% of an entire length of a protein that is at least 95% identical to SEQ ID NO: 3.

In some embodiments, the vaccine comprises a synthetic consensus Survivin antigen, wherein the antigen comprises SEQ ID NO: 4; a fragment comprising at least 90% of the length of SEQ ID NO 4; an amino acid sequence that is at least 95% identical to SEQ ID NO: 4; or a fragment comprising at least 90% of an entire length of a protein that is at least 95% identical to SEQ ID NO: 4.

The vaccines can be used to protect against cancer, for example, a cancer or tumor expressing Survivin. The vaccines can be used to prevent and/or treat a tumor expressing Survivin in a subject in need thereof. The vaccines can induce cellular and/or antibody responses against Survivin and against tumors expressing Survivin.

In one embodiment, the vaccines can be used to protect against, to prevent and/or treat, or to induce a cellular and/or antibody response against ovarian cancer cells expressing Survivin, specifically epithelial ovarian cancer cells expressing Survivin, more specifically serous ovarian cancer cells expressing Survivin.

The development of a cancer vaccine as described herein comprises identifying a cancer antigen, e.g., Survivin, that is not recognized by the immune system and is a tumor-associated ("cancer/testis," "C/T") antigen. The cancer antigen identified is changed from a self-antigen to a foreign antigen in order to be recognized by the immune system. The redesign of the nucleic acid and amino acid sequence of the recombinant cancer antigen from a self to a foreign antigen breaks tolerance of the antigen by the immune system. In order to break tolerance, several redesign measures can be applied to the cancer antigen as described below.

The recombinant cancer antigen of the vaccine is not recognized as self, thereby breaking tolerance. The breaking of tolerance can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-7) and/or tumor necrosis factor alpha (TNF-α) and/or interleukin 2 (IL-2). In other embodiments, the induced or elicited immune response can reduce or inhibit one or more immune suppression factors that promote growth of the tumor or cancer expressing the antigen, for example, but not limited to, factors that down-regulate MHC presentation, factors that upregulate antigen-specific regulatory T cells (Tregs), PD-L1, FasL, cytokines such as IL-10 and TFG-0, tumor associated macrophages, tumor associated fibroblasts, soluble factors produced by immune suppressor cells, CTLA-4, PD-1, MDSCs, MCP-1, and an immune checkpoint molecule.

In a particular embodiment, the vaccine can mediate clearance or prevent growth of tumor cells by (1) increasing cytotoxic T lymphocyte such as CD8+ and/or CD107a+ (CTL) to attack and kill tumor cells; (2) increasing T helper cell responses; and/or (3) increasing inflammatory responses via IFN-7, IL-2, and TFN-α, or preferably all of the aforementioned.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can include an RNA encoding the cancer antigen. The RNA vaccine can be introduced into the cell.

The vaccine can be an attenuated live vaccine, a vaccine using recombinant vectors to deliver antigen, subunit vaccines, and glycoprotein vaccines, for example, but not limited to, the vaccines described in U.S. Pat. Nos. 4,510, 245; 4,797,368; 4,722,848; 4,790,987; 4,920,209; 5,017, 487; 5,077,044; 5,110,587; 5,112,749; 5,174,993; 5,223, 424; 5,225,336; 5,240,703; 5,242,829; 5,294,441; 5,294, 548; 5,310,668; 5,387,744; 5,389,368; 5,424,065; 5,451, 499; 5,453,364; 5,462,734; 5,470,734; 5,474,935; 5,482, 713; 5,591,439; 5,643,579; 5,650,309; 5,698,202; 5,955, 088; 6,034,298; 6,042,836; 6,156,319 and 6,589,529, which are each incorporated herein by reference.

In some embodiments, the nucleic acid vaccine may further comprise coding sequence for a molecular adjuvant, in some cases the molecular adjuvant can be IL-12, IL-15, IL-28, IL-31, IL-33, and/or RANTES, and in some cases the molecular adjuvant is a checkpoint inhibitor, including anti-cytotoxic T-lymphocyte antigen 4 (CTLA-4), anti-programmed death receptor-1 (PD-1) and anti-lymphocyte-activation gene (LAG-3). Coding sequence for IL-12, IL-15, IL-28, IL-31, IL-33 and/or RANTES may be included on one or more nucleic acid molecules that comprise coding sequence for one or more antigens. Coding sequence for IL-12, IL-15, IL-28, IL-31, IL-33 and/or RANTES may be included on one or more separate nucleic acid molecules such as one or more separate plasmids or vectors and administered in combination with the nucleic acid vaccine.

The vaccines of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by containing the nucleic acid molecule(s) encoding the cancer antigen as discussed below.

Vaccine in Combination with Immune Checkpoint Inhibitor

The vaccine can further comprise one or more inhibitors of one or more immune checkpoint molecules (i.e., an immune checkpoint inhibitor). Immune checkpoint molecules are described below in more detail. The immune checkpoint inhibitor is any nucleic acid or protein that prevents the suppression of any component in the immune system such as NMC class presentation, T cell presentation and/or differentiation, B cell presentation and/or differentiation, any cytokine, chemokine or signaling for immune cell proliferation and/or differentiation.

Such an inhibitor can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

In some embodiments, the immune checkpoint inhibitor can be one or more nucleic acid sequences encoding an antibody, a variant thereof, a fragment thereof, or a combination thereof. In other embodiments, the immune checkpoint inhibitor can be an antibody, a variant thereof, a fragment thereof, or a combination thereof.

Immune Checkpoint Molecule

The immune checkpoint molecule can be a nucleic acid sequence, an amino acid sequence, a small molecule, or a combination thereof. The nucleic acid sequence can be DNA, RNA, cDNA, a variant thereof, a fragment thereof, or a combination thereof. The nucleic acid can also include additional sequences that encode linker or tag sequences that are linked to the immune checkpoint inhibitor by a peptide bond. The small molecule may be a low molecular weight, for example, less than 800 Daltons, organic or inorganic compound that can serve as an enzyme substrate, ligand (or analog thereof) bound by a protein or nucleic acid, or regulator of a biological process. The amino acid sequence can be protein, a peptide, a variant thereof, a fragment thereof, or a combination thereof.

PD-1 and PD-L1

The immune checkpoint molecule may programmed cell death protein 1 (PD-1), programmed cell death ligand 1 (PD-L1), a fragment thereof, a variant thereof, or a combination thereof. PD-1 is a cell surface protein encoded by the PDCD1 gene. PD-1 is a member of the immunoglobulin superfamily and is expressed on T cells and pro-B cells, and thus, contributes to the fate and/or differentiation of these cells. In particular, PD-1 is a type 1 membrane protein of the CD28/CTLA-4 family of T cell regulators and negatively regulates T cell receptor (TCR) signals, thereby negatively regulating immune responses. PD-1 can negatively regulated CD8+ T cell responses, and thus inhibit CD8-mediated cytotoxicity and enhance tumor growth.

PD-1 has two ligands, PD-L1 and PD-L2, which are members of the B7 family. PD-L1 is upregulated on macrophages and dendritic cells (DCs) in response to LPS and GM-CSF treatment and on T cells and B cells upon TCR and B cell receptor signaling. PD-L1 is expressed by many tumor cell lines, including myelomas, mastocytomas, and melanomas.

Anti-Immune Checkpoint Molecule Antibody

As described above, the immune checkpoint inhibitor can be an antibody. The antibody can bind or react with an antigen (i.e., the immune checkpoint molecule described above.) Accordingly, the antibody may be considered an anti-immune checkpoint molecule antibody or an immune checkpoint molecule antibody. The antibody can be encoded by a nucleic acid sequence contained in The antibody can include a heavy chain polypeptide and a light chain polypeptide. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

The light chain polypeptide can include a variable light chain (VL) region and/or a constant light chain (CL) region. The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

Additionally, the proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

PD-1 Antibody

The anti-immune checkpoint molecule antibody can be an anti-PD-1 antibody (also referred to herein as "PD-1 antibody"), a variant thereof, a fragment thereof, or a combination thereof. The PD-1 antibody can be Nivolumab. The anti-PD-1 antibody can inhibit PD-1 activity, thereby inducing, eliciting, or increasing an immune response against a tumor or cancer and decreasing tumor growth.

PD-L1 Antibody

The anti-immune checkpoint molecule antibody can be an anti-PD-L1 antibody (also referred to herein as "PD-L1 antibody"), a variant thereof, a fragment thereof, or a combination thereof. The anti-PD-L1 antibody can inhibit PD-L1 activity, thereby inducing, eliciting, or increasing an immune response against a tumor or cancer and decreasing tumor growth.

Antigens

As described above, the vaccine can comprise an antigen or a nucleic acid encoding an antigen. The antigen can be Survivin, a fragment thereof, a variant thereof, or a combination of a fragment and a variant thereof.

Accordingly, the vaccine can be used for treating subjects suffering from cancers or tumors that express Survivin. In some embodiments, the cancer is ovarian cancer. In some embodiments, the ovarian cancer is epithelial ovarian cancer. The ovarian cancer may be serous epithelial ovarian cancer. The vaccine can also be used for treating subjects with cancers or tumors that express Survivin for preventing development of such tumors in subjects. The synthetic consensus Survivin antigen can differ from the native, Survivin gene, and thus provide therapy or prophylaxis against a synthetic consensus Survivin antigen-expressing tumor. Accordingly, synthetic consensus Survivin antigen sequences that differ from the native Survivin gene (i.e., mutated or synthetic Survivin genes or sequences) are provided herein.

Transcripts of the native Survivin gene are processed into a variety of mRNAs. Particular Survivin mRNA isoforms can be selected based, for example, on their expression in cancer cells. In particular embodiments, the Survivin isoform is selected based on its expression in ovarian cancer cells. The synthetic consensus Survivin antigen sequences described herein avoid alternative processing, producing one full-length transcript and resulting in stronger induction of effector T and B cell responses.

Isolated nucleic acid molecules comprising the above-described heterologous sequences are provided. Isolated nucleic acid molecules consisting of the above-described heterologous sequences are provided. Isolated nucleic acid molecules comprising the above-described heterologous sequences may be incorporated into vectors such as plasmids, viral vectors and other forms of nucleic acid molecules as described below. Provided herein are nucleic acid sequences that encode synthetic consensus Survivin antigens. Coding sequences encoding synthetic consensus Survivin antigens have the sequences as described above.

Protein molecules comprising the above-described heterologous amino acid sequences are provided. Protein molecules consisting of the above-described heterologous amino acid sequences are provided. Provided herein are proteins and polypeptides having the above-described sequences. The proteins and polypeptide may be referred to as synthetic consensus Survivin antigens and Survivin immunogens. Synthetic consensus Survivin antigens are capable of eliciting an immune response against tumors expressing Survivin.

In one aspect, it is desired that the synthetic consensus Survivin antigen provide for improved transcription and translation, including having one or more of the following: low GC content leader sequence to increase transcription; mRNA stability and codon optimization; and, to the extent possible, elimination of cis-acting sequence motifs (i.e., internal TATA-boxes).

The synthetic consensus Survivin antigen can be a consensus antigen (or immunogen) sequence derived from two or more species, isoforms, or variants. In one embodiment, a consensus sequence is generated from Survivin isoforms of different species. The consensus sequence is derived from Survivin sequences collected from GenBank or other similar DNA or protein sequence database. In some embodiments, the consensus antigen can comprise a portion of a first isoform combined with a portion of a second isoform, the portion of the second isoform, for example, being non-homologous with any portion of the first isoform. The synthetic consensus Survivin antigen can comprise a consensus sequence and/or modification(s) for improved expression. Modification can include codon optimization, RNA optimization, addition of a kozak sequence (e.g., GCC ACC) for increased translation initiation and/or the addition of an immunoglobulin leader sequence to increase the immunogenicity of the synthetic consensus Survivin antigen. The synthetic consensus Survivin antigen can comprise a signal peptide such as an immunoglobulin signal peptide, for example, but not limited to, an immunoglobulin E (IgE) or immunoglobulin G (IgG) signal peptide. In some embodiments, the synthetic consensus Survivin antigen can include mutations or deletions to localization signal sequences, e.g., a nuclear localization signal for example to disrupt nuclear localization upon translation. In some embodiments, the Survivin consensus antigen can comprise a hemagglutinin (HA) tag. The Survivin consensus antigen can be designed to elicit stronger and broader cellular and/or humoral immune responses than a corresponding non-codon-optimized Survivin antigen.

The consensus Survivin sequence can be mutated to disrupt and/or to enhance particular structures and/or functions of native Survivin to produce a synthetic consensus Survivin antigen sequence. In one embodiment, mutations are introduced to abolish anti-apoptotic activity of Survivin. In a particular embodiment, T34A, T48A, and C84A mutations are introduced into the consensus Survivin isoform 1 sequence to abolish anti-apoptotic function. (See Muchmore, S. W. et al. Crystal structure and mutagenic analysis of the inhibitor-of-apoptosis protein Survivin. Molecular cell 6, 173-182 (2000); O'Connor, D. S. et al. Regulation of apoptosis at cell division by p34cdc2 phosphorylation of Survivin. Proceedings of the National Academy of Sciences of the United States of America 97, 13103-13107 (2000); Barrett, R. M., Colnaghi, R. & Wheatley, S. P. Threonine 48 in the BIR domain of Survivin is critical to its mitotic and anti-apoptotic activities and can be phosphorylated by CK2 in vitro. Cell cycle (Georgetown, Tex.) 10, 538-548 (2011).)

In some embodiments, the synthetic consensus Survivin antigen sequence can be generated from one isoform, for example the dominant Survivin isoform, or the consensus sequence can comprise a combination of a portion of a first isoform and a portion of a second isoform, or a truncated portion of a second isoform. In one embodiment, the synthetic consensus sequence is derived from Suvivin isoform 1 (Survivin 1). In another embodiment, the synthetic consensus sequence is derived from Survivin isoform 3 (Survivin 3). In one embodiment, the synthetic consensus Survivin antigen 3 sequence is a truncated portion of Survivin 3 (Survivin 3T). In one embodiment, the synthetic consensus sequence is a combination of Survivin 1 and Survivin T3, or Survivin 1T3.

In a preferred embodiment, the synthetic consensus Survivin antigen sequence shares 95.0% or more identity with SEQ ID NO:1 or SEQ ID NO:3. In this embodiment, the nucleic acid sequence of SEQ ID NO:1 or SEQ ID NO:3 encodes an amino acid sequence of SEQ ID NO:2 or SEQ ID NO:8, respectively. In other embodiments, the synthetic consensus Survivin antigen sequence shares 95.0% or more identity, 95.2% or more identity, 95.4% or more identity, 95.6% or more identity, 95.8% or more identity, 96.0% or more identity, 96.2% or more identity, 96.4% or more identity, 96.6% or more identity, 96.8% or more identity, 97.0% or more identity, 97.2% or more identity, 97.4% or more identity, 97.6% or more identity, 97.8% or more identity, 98.0% or more identity, 98.2% or more identity, 98.4% or more identity, or 98.6% or more identity, 98.8% or more identity, 99.0% or more identity, 99.2% or more identity, 99.4% or more identity, 99.6% or more identity, 99.8% or more identity, or 100% identity with SEQ ID NO:1 or SEQ ID NO:3.

Vectors

The vaccine can comprise one or more vectors that include a heterologous nucleic acid encoding the synthetic consensus Survivin antigen. The one or more vectors can be capable of expressing the antigen in a quantity effective to elicit an immune response in the mammal. The vector may comprise heterologous nucleic acid encoding the antigen. The vector can have a nucleic acid sequence containing an origin of replication. The vector can be a plasmid, bacteriophage, bacterial artificial chromosome or yeast artificial chromosome. The vector can be either a self-replication extra chromosomal vector, or a vector that integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence as well as sequences for cloning and subcloning the vector and fragments thereof. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development. In a preferred embodiment, the plasmid vector is pGX1428 described herein, further comprising the nucleic acid sequence of SEQ ID NO:1; or pGX1429 described herein, further comprising the nucleic acid sequence of SEQ ID NO:3.

The vector can be a plasmid. The plasmid may be useful for transfecting cells with nucleic acid encoding the antigen. The transformed host cells can be cultured and maintained under conditions wherein expression of the antigen takes place.

The plasmid may comprise a nucleic acid sequence that encodes one or more of the various antigens disclosed above including coding sequences that encode synthetic, consensus antigen capable of eliciting an immune response against an antigen, fragments of such proteins, variants of such proteins, fragments of variants or fusion proteins which are made up of combinations of consensus proteins and/or fragments of consensus protein and/or variants of consensus protein and/or fragments of variants of consensus proteins.

A single plasmid may contain coding sequence for a single antigen, coding sequence for two antigens, coding sequence for three antigens or coding sequence for four antigens.

In some embodiments, a plasmid may further comprise coding sequence that encodes CCR20 alone or as part of one these plasmids. Similarly, plasmids may further comprise coding sequences for IL-12, IL-15 and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metallothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pA V0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif), which may be used for protein production in *Escherichia coli* (*E. coli*). The plasmid may also be p YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif), which may be used for protein production in insect cells. The plasmid may also be pcDNA I or pcDNA3 (Invitrogen, San Diego, Calif.), which may be used for protein production in mammalian cells such as Chinese hamster ovary (CHO) cells.

The vector may be circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be pcrM2. The LEC can be pcrNP. pcrNP and pcrMR can be derived from pNP (Puerto Rico/34) and pM2 (New Caledonia/99), respectively.

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

Methods of Preparing the Vector

Provided herein are methods for preparing the vector that comprises the synthetic consensus Survivin antigen-encoding nucleic acid molecules discussed herein. The vector, after the final subcloning step, can be used to inoculate a cell culture in a large-scale fermentation tank, using known methods in the art.

The vector for use with the EP devices, which are described below in more detail, can be formulated or manufactured using a combination of known devices and techniques, but preferably they are manufactured using an optimized plasmid manufacturing technique that is described in U.S. provisional application U.S. Ser. No. 60/939,792, which was filed on May 23, 2007 (see U.S. Pat. Pub. No. 20090004716). In some examples, the DNA vectors used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939, 792, including those described in U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Excipients and other Components of the Vaccine

The vaccine may further comprise a pharmaceutically acceptable excipient. The pharmaceutically acceptable excipient can be a functional molecule such as a vehicle, carrier, or diluent. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection-facilitating agent is a polyanion, polycation, including poly-L-glutamate (LGS), or lipid. The transfection-facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA vector vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection-facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be one or more adjuvants. The adjuvant can be other genes that are expressed in an alternative vector or are delivered as proteins in combination with the vector above in the vaccine. The one or more adjuvants may be selected from the group consisting of: CCL20, α-interferon(IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHIC, CD80, CD86, IL-1, IL-2, IL-4, IL-5, IL-6, IL-10, IL-18, IL-33, MCP-1, MIP-1a, MIP-1~, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, INK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2, IL-15 having the signal sequence or coding sequence that encodes the signal sequence deleted and optionally including a different signal peptide such as that from IgE or coding sequence that encodes a different signal peptide such as that from IgE, and functional fragments thereof, or a combination thereof. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

In some embodiments, adjuvant may be one or more nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/USI0/048827, which are each incorporated herein by reference. Examples ofiL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

Other genes that can be useful as adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, INK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine may comprise the plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, vaccine according to the present invention comprise about 5 nanogram to about 1000 micrograms of DNA. In some preferred embodiments, vaccine can contain about 10 nanograms to about 800 micrograms of DNA. In some preferred embodiments, the vaccine can contain about 0.1 to about 500 micrograms of DNA. In some preferred embodiments, the vaccine can contain about 1 to about 350 micrograms of DNA. In some preferred embodiments, the vaccine can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the antigen or plasmid encoding the same.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

Pharmaceutical Compositions of the Vaccine

The vaccine can be in the form of a pharmaceutical composition. The pharmaceutical composition can comprise the vaccine. The pharmaceutical compositions can comprise about 5 nanograms (ng) to about 10 milligrams (mg) of the nucleic acid molecule(s) of the vaccine. In some embodiments, pharmaceutical compositions according to the present invention comprise about 25 ng to about 5 mg the nucleic acid molecule(s) of the vaccine. In some embodiments, pharmaceutical compositions contain about 50 ng to about 1 mg the nucleic acid molecule(s) of the vaccine. In some embodiments, the pharmaceutical compositions contain about 0.1 to about 500 micrograms of the nucleic acid molecule(s) of the vaccine. In some embodiments, the pharmaceutical compositions contain about 1 to about 350 micrograms of the nucleic acid molecule(s) of the vaccine. In some embodiments, the pharmaceutical compositions contain about 5 to about 250 micrograms of the nucleic acid molecule(s) of the vaccine. In some embodiments, the pharmaceutical compositions contain about 10 to about 200 micrograms of the nucleic acid molecule(s) of the vaccine. In some embodiments, the pharmaceutical compositions contain about 15 to about 150 micrograms of the nucleic acid molecule(s) of the vaccine. In some embodiments, the pharmaceutical compositions contain about 20 to about 100 micrograms of the nucleic acid molecule(s) of the vaccine. In some embodiments, the pharmaceutical compositions contain about 25 to about 75 micrograms of the nucleic acid molecule(s) of the vaccine. In some embodiments, the pharmaceutical compositions contain about 30 to about 50 micrograms of the nucleic acid molecule(s) of the vaccine. In some embodiments, the pharmaceutical compositions contain about 35 to about 40 micrograms of the nucleic acid molecule(s) of the vaccine. In some embodiments, the pharmaceutical compositions contain about 100 to about 200 micrograms of the nucleic acid molecule(s) of the vaccine. In some embodiments, the pharmaceutical compositions comprise about 10 micrograms to about 100 micrograms of the nucleic acid molecule(s) of the vaccine. In some embodiments, the pharmaceutical compositions comprise about 20 micrograms to about 80 micrograms of the nucleic acid molecule(s) of the vaccine. In some embodiments, the pharmaceutical compositions comprise about 25 micrograms to about 60 micrograms of the nucleic acid molecule(s) of the vaccine. In some embodiments, the pharmaceutical compositions comprise about 30 ng to about 50 micrograms of the nucleic acid molecule(s) of the vaccine. In some embodiments, the pharmaceutical compositions comprise about 35 ng to about 45 micrograms of the nucleic acid molecule(s) of the vaccine. In some preferred embodiments, the pharmaceutical compositions contain about 0.1 to about 500 micrograms of the nucleic acid molecule(s) of the vaccine. In some preferred embodiments, the pharmaceutical compositions contain about 1 to about 350 micrograms of the nucleic acid molecule(s) of the vaccine. In some preferred embodiments, the pharmaceutical compositions contain about 25 to about 250 micrograms of the nucleic acid molecule(s) of the vaccine. In some preferred embodiments, the pharmaceutical compositions contain about 100 to about 200 micrograms of the nucleic acid molecule(s) of the vaccine.

In some embodiments, pharmaceutical compositions according to the present invention comprise at least 10, 15, 20, 25, 30, 35, 40, 45, 50, 55, 60, 65, 70, 75, 80, 85, 90, 95 or 100 ng the nucleic acid molecule(s) of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms of the nucleic acid molecule(s) of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more the nucleic acid molecule(s) of the vaccine.

In other embodiments, the pharmaceutical composition can comprise up to and including 15, 20, 25, 30, 35, 40, 45, 50, 55, 60, 65, 70, 75, 80, 85, 90, 95 or 100 ng the nucleic acid molecule(s) of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms of the nucleic acid molecule(s) of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg the nucleic acid molecule(s) of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The pharmaceutical composition can further comprise a pharmaceutically acceptable excipient as provided above in Section 2. For example, the pharmaceutically acceptable excipient can comprise the functional molecules, vehicles, adjuvants, carriers, diluents, or transfection facilitating agents, as provided in Section 2.

Indications

The vaccines and the pharmaceutical compositions comprising the vaccines provided herein can be used in the treatment or prevention of cancer cells and cancer-based tumors expressing Survivin. In particular, the vaccines and the pharmaceutical compositions comprising the vaccines provided herein can be used in the treatment or prevention of ovarian cancer, more particularly epithelial ovarian cancer, most particularly serous ovarian cancer.

Methods of Vaccination

Provided herein are methods for treating and/or preventing cancer using the pharmaceutical formulations described above. Also described herein are methods of using the pharmaceutical formulations described above in the treatment and/or prevention of cancer in a subject. Also described herein are methods of vaccinating a subject. Also described herein are methods of administering the pharmaceutical formulations described herein to a subject in need thereof. The methods described herein collectively referred to as methods of treatment using the pharmaceutical formulations described herein can comprise administering one or more vaccine as described herein to a subject in need thereof to induce a therapeutic and/or prophylactic immune response. The vaccine can be administered to a subject to modulate the activity of the subject's immune system and enhance the immune response. The administration of the vaccine can be the transfection of the cancer antigens as disclosed herein as a nucleic acid molecule that is expressed in the cell and delivered to the surface of the cell, whereupon the immune system recognizes and induces a cellular, humoral, or cellular and humoral response. The administration of the vaccine can be used to induce or elicit an immune response in subjects against one or more of the cancer antigens as disclosed herein by administering to the subject the vaccine as discussed herein.

The vaccine can be administered to a subject to modulate the activity of the subject's immune system, thereby enhancing the immune response. In some embodiments, the subject is a mammal. Upon administration of the vaccine to the mammal, and thereby introducing the vector into the cells of the mammal, the transfected cells will express and secrete one or more of the cancer antigens as disclosed herein. These secreted proteins, or synthetic antigens, will be recognized as foreign by the immune system, which will mount an immune response that can include: antibodies made against the one or more cancer antigens, and T-cell response specifically against the one or more cancer antigens. In some examples, a mammal vaccinated with the vaccines discussed herein will have a primed immune system and when challenged with the one or more cancer antigens as disclosed herein, the primed immune system will allow for rapid clearing of subsequent cancer antigens as disclosed herein, whether through the humoral, cellular, or both cellular and humoral immune responses.

Methods of administering the DNA of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, and preferably human, cow, or pig. The vaccine can likewise be administered to a non-mammal subject, for example, a chicken, to elicit an immune response.

The vaccine dose can be between 1 microgram and 10 mg active component per kilogram (kg) body weight over time (component/kg body weight/time), and can be 20 micrograms to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

Methods of Generating an Immune Response with the Vaccine

The vaccine can be used to generate an immune response in a mammal or non-mammal subject, including therapeutic or prophylactic immune response. The immune response can generate antibodies and/or killer T cells directed to the one or more cancer antigens as disclosed herein. Such antibodies and T cells can be isolated.

Some embodiments provide methods of generating immune responses against one or more of the cancer antigens as disclosed herein, which embodiments comprise administering the vaccine to a subject. Some embodiments provide methods of prophylactically vaccinating a subject against a cancer or tumor expressing one or more of the cancer antigens as described above, which embodiments comprise administering the vaccine. Some embodiments provide methods of therapeutically vaccinating a subject that has been suffering from the cancer or tumor expressing one or more of the cancer antigens, which embodiments comprise administering the vaccine. Diagnosis of the cancer or tumor expressing the one or more cancer antigens as disclosed herein prior to administration of the vaccine can be done routinely.

Methods of Cancer Treatment with the Vaccine

The vaccine can be used to generate or elicit an immune response in a mammal that is reactive or directed to a Survivin-expressing cancer or tumor (e.g., ovarian cancer) of the mammal or subject in need thereof. The elicited immune response can prevent cancer or tumor growth.

The elicited immune response can prevent and/or reduce metastasis of cancerous or tumor cells. Accordingly, the vaccine can be used in a method that treats and/or prevents cancer or tumors in the mammal or subject administered the vaccine.

Routes of Administration

The vaccine or pharmaceutical composition can be administered by different routes including orally, parenterally, sublingually, transdermally, rectally, transmucosally, topically, via inhalation, via buccal administration, intrapleurally, intravenously, intraarterially, intraperitoneally, subcutaneously, intramuscularly, intranasal intrathecally, and/or intraarticularly, or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gene guns", or other physical methods such as electroporation ("EP"), "hydrodynamic method", or ultrasound.

The vector of the vaccine can be administered to the mammal by several well-known technologies including DNA injection (also referred to as DNA vaccination) with and without in vivo electroporation, liposome mediated transfection, nanoparticle facilitated transfection, and use recombinant vectors such as recombinant adenovirus, recombinant adenovirus associated virus, and recombinant vaccinia. The one or more cancer antigens of the vaccine can be administered via DNA injection along with in vivo electroporation.

The vaccine or pharmaceutical composition comprising the vaccine can be administered by electroporation. Administration of the vaccine via electroporation can be accomplished using electroporation devices that can be configured to deliver to a desired tissue of a mammal a pulse of energy effective to cause reversible pores to form in cell membranes, and preferably the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, PA) or Elgen electroporator (Inovio Pharmaceuticals, Inc.) to facilitate transfection of cells by the vector.

Examples of electroporation devices and electroporation methods that can facilitate administration of the DNA vaccines of the present invention include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating administration of the DNA vaccines include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then administering via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference in its entirety.

U.S. Patent Pub. 2005/0052630 submitted by Smith, et al. describes an electroporation device that can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby fully incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns administration of DNA using any of a variety of devices, and U.S. Pat. No. 7,328,064 issued Feb. 5, 2008, drawn to method of injecting DNA are contemplated herein. The above-patents are incorporated by reference in their entirety.

Provided herein are methods for preparing the vectors that comprise the nucleic acid molecule(s) encoding synthetic consensus Survivin antigen discussed herein. The vectors, after the final subcloning step into the mammalian expression plasmid, can be used to inoculate a cell culture in a large-scale fermentation tank, using known methods in the art.

The DNA vectors for use with the EP devices of the present invention can be formulated or manufactured using a combination of known devices and techniques, but preferably they are manufactured using an optimized manufacturing technique that is described in US published application no. 20090004716, which was filed on May 23, 2007. In some examples, the DNA vectors used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1—Generation of Consensus Survivin Isoform 1

Twenty-nine Survivin isoform 1 sequences were collected from GenBank. The GenBank accession numbers for selected Survivin isoform 1 sequences are: NP_001125727.1, 3UIG, 1F3H, BAC22748.2, NP_001159.2, CAG46540.1, BAD97148.1, XP_002748841.1, XP_003818322.1, NP_001253110.1, XP_011810718.1, XP_011832690.1, XP_001083183.1, XP_003786134.1, XP_012516801.1, XP_007957800.1, XP_001915435.1, XP_008523102.1, AAT37504.1, XP_004432883.1, XP_003417277.1, XP_004374167.1, NP_999306.1, XP_002918421.1, NP_001003348.1, NP_001009280.1, XP_004748859.1, NP_001001855.2, and AAU89275.1.

A consensus sequence was generated using the DNASTAR® Lasergene software package (version 13.0.0.357). The twenty-nine sequences listed above were imported into MegAlign and aligned using the ClustalW multiple sequence alignment program. The resulting consensus Survivin isoform 1 sequence shares 97.2-97.9% homology with native human Survivin isoform 1. In order to abolish the potential biological function of the resulting consensus Survivin isoform 1 protein, three mutations were introduced to abolish the anti-apoptotic activity of Survivin. The three mutations are T34A, T48A, and C84A. Further, in order to have a higher level of expression, an upstream Kozak sequence and IgE leader sequence were added to the N-terminus. Furthermore, the codon usage of this gene was adapted to the codon bias of *Homo sapiens* genes. (Andre, S. et al. Increased immune response elicited by DNA vaccination with a synthetic gp120 sequence with optimized codon usage. Journal of virology 72, 1497-1503 (1998); Deml, L. et al. Multiple effects of codon usage optimization on expression and immunogenicity of DNA candidate vaccines encoding the human immunodeficiency virus type 1 Gag protein. Journal of virology 75, 10991-11001 (2001)). In addition, RNA optimization was also performed: regions of very high (>80%) or very low (<30%) GC content and the cis-acting sequence motifs such as internal TATA boxes, chi-sites and ribosomal entry sites were avoided. As a result, the synthetic consensus Survivin antigen isoform 1 protein shares 95.1-95.8% identity with human native Survivin isoform 1 protein. The nucleotide sequence of synthetic consensus Survivin antigen isoform 1 is set forth in SEQ ID NO: 1. The amino acid sequence of synthetic consensus Survivin antigen isoform 1 is set forth in SEQ ID NO: 2.

Figure 2:
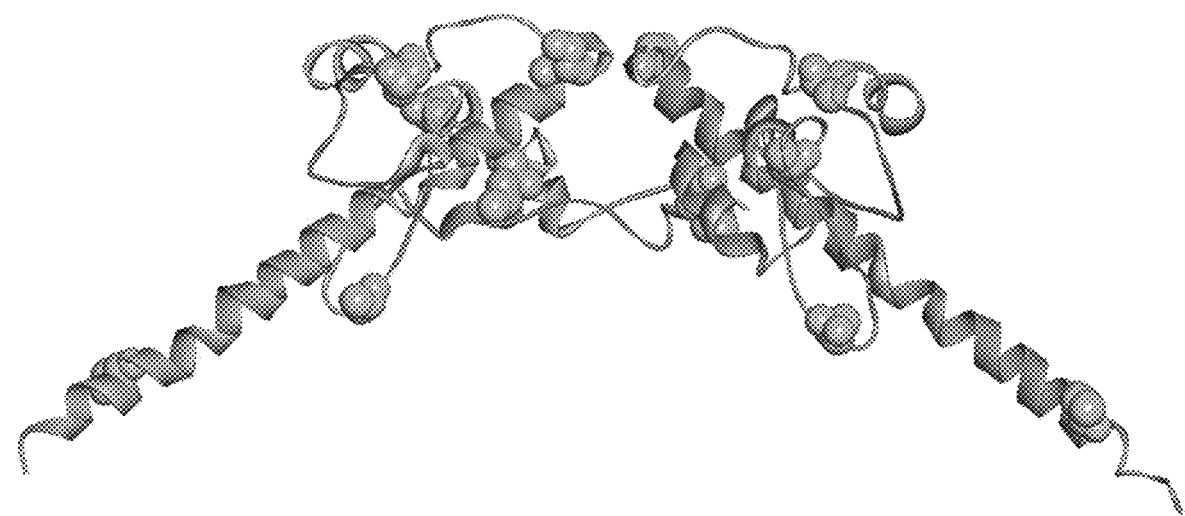
FIG. 2 shows the overall structure of synthetic consensus Survivin antigen isoform 1 monomer A (left) and monomer B (right). Changes relative to native Survivin are designated by spheres.

The synthetic consensus Survivin antigen isoform 1 was digested with BamH and XhoI, and cloned into proprietary expression vector pGX0001 with the expression cassette placed under the transcription control of the cytomegalovirus immediate-early promoter. The resulting plasmid was designated pGX1428. Full length sequencing was performed and then analyzed and confirmed to be correct. A schematic representation of the synthetic consensus Survivin antigen isoform 1 construct is shown in FIG. 1. The overall structure of synthetic consensus Survivin antigen isoform 1 is shown in FIG. 2.

TABLE 1

| Feature | Amino acid position |
|---|---|
| Features of SEQ ID NO: 3 | |
| IgE leader sequence | 1-18 |
| Survivin coding sequence | 19-159 |
| Mutations to abolish anti-apoptotic activity | T51A |
| | T65A |
| | C101A |
| Features of SEQ ID NO: 8 | |
| IgE leader sequence | 1-18 |
| Survivin isoform 1 coding sequence | 19-161 |
| Mutations to abolish anti-apoptotic activity | T51A |
| | T65A |
| | C101A |
| Furin cleavage site | 160-166 |
| Truncated Survivin isoform 3 coding sequence | 167-232 |

TABLE 2

Characteristics of synthetic consensus Survivin antigen isoform 1

| Characteristics | synthetic consensus Survivin antigen isoform 1 |
|---|---|
| Identity to native human Survivin | 95.1% to 95.8% |
| Identity to native rhesus Survivin | 95.8% |
| Identity to native mouse Survivin | 70.0% to 83.6% |
| Number of amino acid mutations (vs native human) | 6 |
| Number of inserted mutations (not consensus derived) | 3 |
| Molecular weight | 161 aa (18 KDa) |
| Length of coding sequence (bp) | 483 |

Example 2—Generation of Consensus Survivin Isoform 1T3

In order to generate a human consensus Survivin isoform 3, 8 Survivin isoform 3 sequences were collected from GenBank. The GenBank accession numbers for selected Survivin isoform 3 sequences are: NP_001012270.1, XP_008969790.1, XP_008011275.1, XP_009189614.1, XP_011897653.1, XP_011810642.1, XP_011844315.1, and XP_011718355.1.

A consensus sequence was generated using the DNASTAR® Lasergene software package (version 13.0.0.357).

The eight sequences listed above were imported into MegAlign and aligned using the ClustalW multiple sequence alignment program. Six of these sequences from lower animals contained an extra 11 amino acid residues at their C-terminal end that are not present in human sequences. These extra residues were omitted when generating the consensus human Survivin isoform 3 to avoid eliciting an off-target immune response in humans. After generating the human consensus Survivin isoform 3, the identical amino acid sequence between Survivin isoform 1 and 3 was removed from the consensus Survivin isoform 3. The truncated consensus Survivin isoform 3 sequence (Survivin antigen T3) shares 96.8% sequence homology with native human Survivin isoform T3 sequence. The Survivin antigen isoform 1T3 immunogen was generated by adding a furin cleavage site between Survivin antigen 1 (described above) and Survivin antigen T3.

Figure 3:
FIG. 3 shows a schematic representation of synthetic consensus Survivin antigen isoform 1T3. Asterisks denote mutations essential for abolishing anti-apoptotic activity. Dark grey region on right (3') represents truncated Survivin Isoform 3 (T3) region.

Once the consensus synthetic consensus Survivin antigen isoform 1T3 DNA sequence was obtained, in order to have a higher level of expression, an upstream Kozak sequence and IgE leader sequence were added to the N-terminus. (Yang, J. S. et al. Induction of potent Th1-type immune responses from a novel DNA vaccine for West Nile virus New York isolate (WNV-NY1999). The Journal of infectious diseases 184, 809-816 (2001)). Furthermore, the codon usage of this gene was adapted to the codon bias of *Homo sapiens* genes (Andre, S. et al. Increased immune response elicited by DNA vaccination with a synthetic gp120 sequence with optimized codon usage. Journal of virology 72, 1497-1503 (1998); Deml, L. et al. Multiple effects of codon usage optimization on expression and immunogenicity of DNA candidate vaccines encoding the human immunodeficiency virus type 1 Gag protein. Journal of virology 75, 10991-11001 (2001)). In addition, RNA optimization was also performed: regions of very high (>80%) or very low (<30%) GC content and the cis-acting sequence motifs such as internal TATA boxes, chi-sites and ribosomal entry sites were avoided11,12. The synthetic consensus Survivin antigen isoform 1T3 was digested with BamHI and XhoI, and cloned into expression vector pGX0001 with the expression cassette placed under the transcription control of the cytomegalovirus immediate-early promoter. The resulting plasmid was designated pGX1429. Full length sequencing was performed and then analyzed and confirmed to be correct. The nucleotide sequence of synthetic consensus Survivin antigen isoform 1T3 is set forth in SEQ ID NO:3, as shown in Table 1. The amino acid sequence of synthetic consensus Survivin antigen isoform 1T3 is set forth in SEQ ID NO:8, as shown in Table 1. A schematic representation of the synthetic consensus Survivin antigen isoform 1T3 construct is shown in FIG. 3. Characteristics of the synthetic consensus Survivin antigen isoform 1T3 construct are provided in Table 3.

TABLE 3

Characteristics of synthetic consensus Survivin antigen isoform 1T3

| Characteristics | synthetic consensus Survivin antigen isoform 1T3 |
|---|---|
| Identity to native human Survivin | 95.1% to 95.8% (iso 1 region); 96.8% (T3 region) |
| Identity to native rhesus Survivin | 95.9% iso 1 region); 9.4% (T3 region) |
| Identity to native mouse Survivin | 70.0% to 84.9% (iso 1 region); 10.9% to 13.0% (T3 region) |
| Number of amino acid mutations (vs native human) | 6 (iso 1 region); 2 (T3 region |
| Number of inserted mutations (not consensus derived) | 3 (iso 1 region); 0 (T3 region) |
| Molecular weight | 232 aa (26 Kda) |
| Length of coding sequence (bp) | 696 |

Example 3—Construction of pGX Survivin Expression Vectors pGX0001 (a modified pVAX1 expression vector) under the control of the human cytomegalovirus immediate-early promoter (hCMV promoter), was used as a backbone vector. The original pVAX1 was obtained from Thermo Fisher Scientific.

Modifications were introduced into pVAX1 to create pGX0001 and are identified based on the reported sequence of pVAX1 available from Thermo Fisher Scientific. These modifications are listed below and no issues have been detected regarding plasmid amplification and antigen transcription and translation. No further changes in the sequence of pGX0001 have been observed to date in any of the plasmid products in the platform using pGX0001 as the backbone.

| Modification | Base Pair | Description |
|---|---|---|
| C > G | 241 | in CMV promoter |
| C > T | 1158 | backbone, downstream of the bovine growth hormone polyadenylation signal (bGH polyA) |
| A > — | 2092 | backbone, downstream of the Kanamycin resistance gene |
| C > T | 2493 | in pUC origin of replication (pUC ori) |
| G > C | 2969 | in very end of pUC On upstream of RNASeH site |

Figure 4:
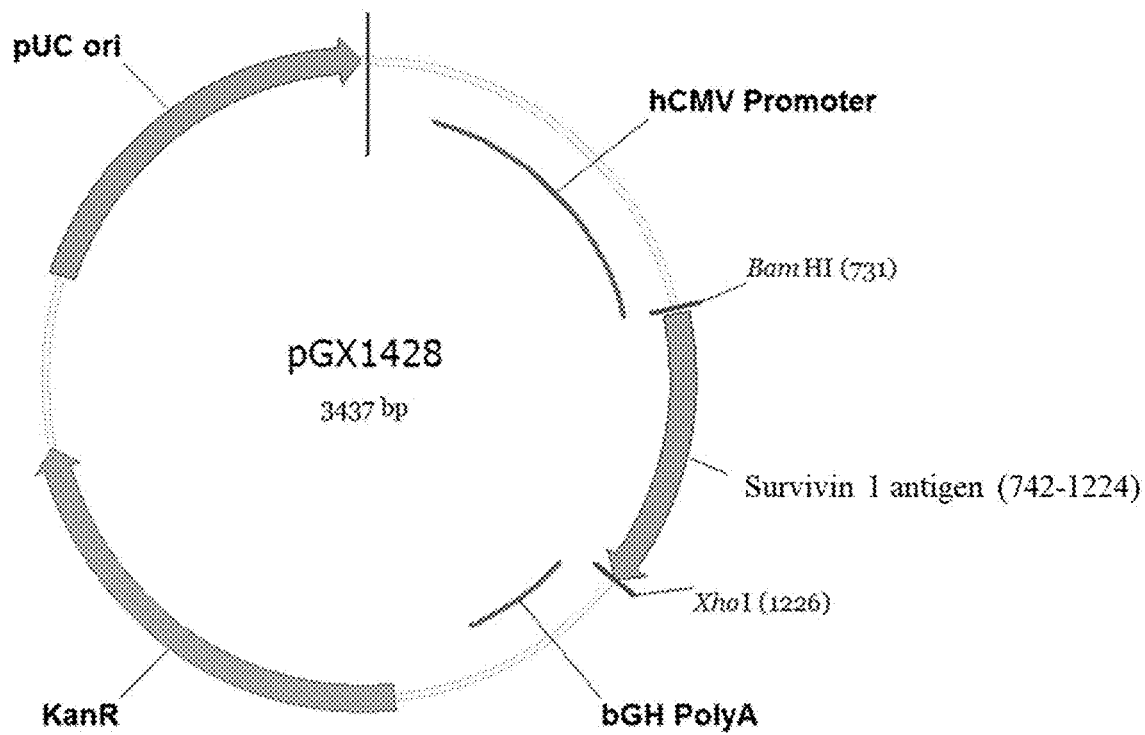
FIG. 4 shows the construction of pGX1428, including synthetic consensus Survivin antigen isoform 1.

Base pairs 2, 3 and 4 are changed from ACT to CTG in backbone, upstream of CMV promoter.

pGX1428 is a DNA plasmid encoding the synthetic consensus Survivin antigen isoform 1 (Survivin antigen 1) protein. Related mRNA production is driven by a human CMV promoter (hCMV promoter) and terminated by the bovine growth hormone 3'end poly-adenylation signal (bGH polyA). The pGX0001 backbone includes the kanamycin resistance gene (KanR) and plasmid origin of replication (pUC ori) for production purpose. Those elements are not functional in eukaryotic cells. pGX1428 was made by cloning the synthetic consensus Survivin antigen isoform 1 (Survivin antigen 1) DNA sequence into pGX0001 at the BamHI and XhoI sites, as illustrated in FIG. 4.

pGX1429 is a DNA plasmid encoding the synthetic consensus Survivin antigen 1T3 (Survivin antigen 1T3) protein. Related mRNA production is driven by a human CMV promoter (hCMV promoter) and terminated by the bovine growth hormone 3'end poly-adenylation signal (bGH polyA). The pGX0001 backbone includes the kanamycin resistance gene (KanR) and plasmid origin of replication (pUC ori) for production purpose. Those elements are not functional in eukaryotic cells. pGX1429 was made by cloning the synthetic consensus Survivin antigen isoform 1T3

Figure 5:
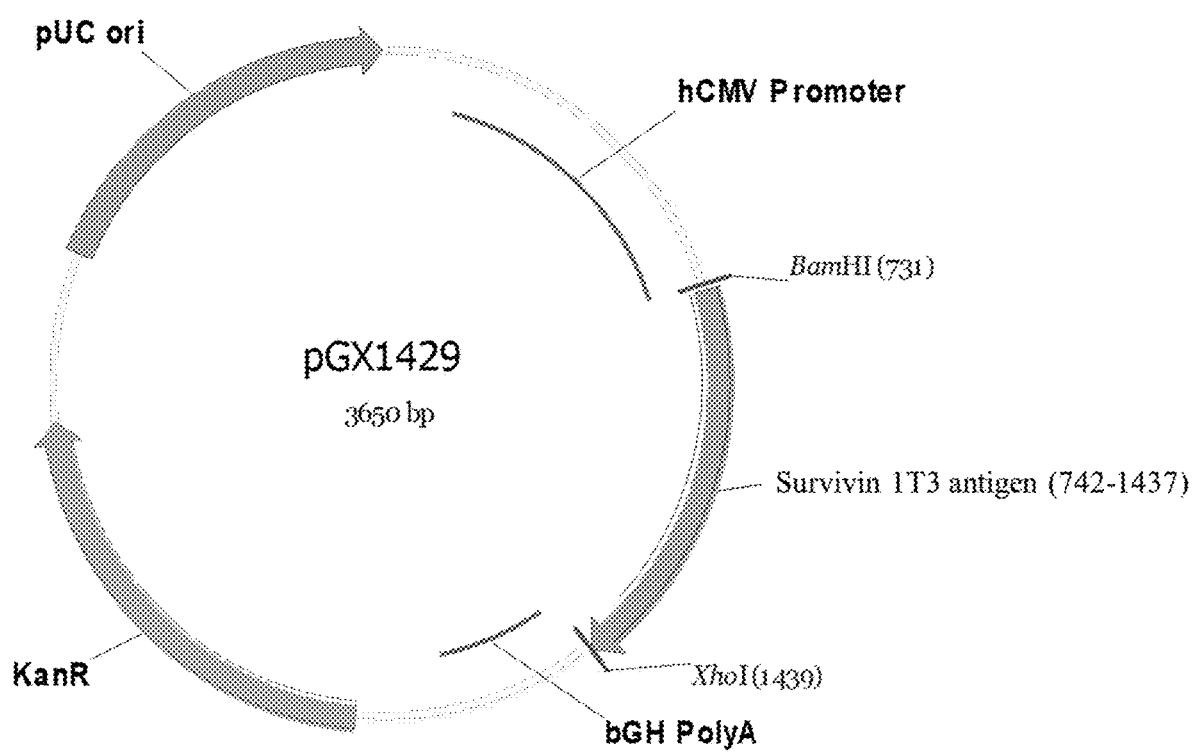
FIG. 5 shows the construction of pGX1429, including synthetic consensus Survivin antigen isoform 1T3.

(Survivin antigen 1T3) DNA sequence into pGX0001 at the BamHI and XhoI sites, as illustrated in FIG. 5.

Example 4—Immunogenicity of Synthetic Consensus Survivin Antigen Constructs

Immunogenicity of the vaccine constructs designed to target human Survivin, synthetic consensus Survivin antigen 1 (pGX1428) and synthetic consensus Survivin antigen 1T3 (pGX1429) was evaluated in mice. Expression of the antigen proteins by each construct was also evaluated in vitro by Western blotting.

Materials and Methods

Plasmids

Synthetic consensus Survivin antigen 1 (pGX1428) and synthetic consensus Survivin antigen 1T3 (pGX1429) were designed as described herein. For in vitro and in vivo studies, plasmids (10 mg) were ordered from GenScript for both pGX1428 (lot #786114S-1/G52238) and pGX1429 (lot #786114S-2/G52239). Antigen sequences of the 10 mg plasmids stocks were confirmed by Sanger sequencing.

In Vitro Antigen Expression

Figure 6:
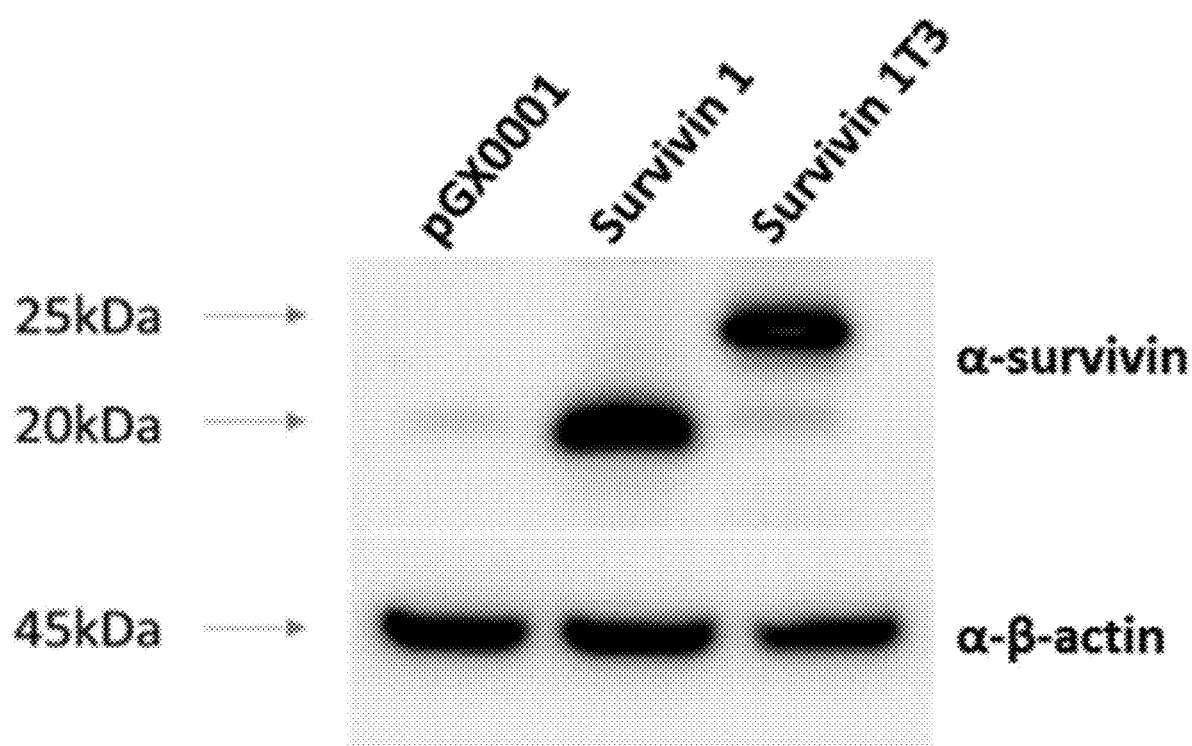
FIG. 6 shows expression of synthetic consensus Survivin antigen 1 and synthetic consensus Survivin antigen 1T3 proteins in human rhabdomyosarcoma (RD) cells transfected with pGX1428 and pGX1429, respectively, by immunoblotting. Protein bands of the expected molecular weights were detected for pGX1428 (17.5 kD) and pGX1429 (25.3 kD). 3-Actin was used as a loading control.

Expression of the antigen proteins by pGX1428 and pGX1429 was confirmed by western blotting. As shown in FIG. 6, Human rhabdomyosarcoma (RD) cells (ATCC, CCL-136) maintained in DMEM medium with 10% FBS (ThermoFisher) were transfected with pGX1428, pGX1429 or pGX0001 (6 µg/10 cm2 dish) using Turbofectin 8 (Origene). Forty-eight hours after transfection, the cells were lysed using RIPA cell lysis buffer (ThermoFisher) and cell lysate was collected. Following a BCA assay (ThermoFisher) to determine total protein concentration, 15 µg of cell lysate was electrophoresed on a 4-12% SDS-PAGE gel (ThermoFisher). Detection was performed with a monoclonal antibody against amino acids 1-142 of human Survivin (Santa Cruz Biotech, clone D8, sc-17779) then visualized with horseradish peroxidase (HRP) conjugated goat anti-mouse IgG (Santa Cruz Biotech, sc-2005) using an ECL western blot analysis system (GE Amersham). As a loading control, blots were re-probed for actin expression using an anti-3-actin monoclonal antibody (Santa Cruz Biotech, clone C4, sc-47778 HRP).

Animals and Immunizations

Female, 8-week-old CB6F1 mice were purchased from Jackson Laboratories. All animals were housed in a temperature-controlled, light-cycled facility at BTS Research (San Diego, CA). Animal care was carried out according to the guidelines of the National Institutes of Health and the Animal Care and Use Proposal (ACUP) (BTS ACUP #15-091). Mice were divided into nine groups as detailed in Table 4.

TABLE 4

Study Groups

| Group | n | Construct | Construct Dose (µg) | Injection volume (µL) |
|---|---|---|---|---|
| 1 | 4 | pGX0001 | 30 | 30 |
| 2 | 8 | pGX1428 | 10 | 30 |
| 3 | 8 | pGX1428 | 20 | 30 |
| 4 | 8 | pGX1428 | 30 | 30 |
| 5 | 8 | pGX1428 | 50 | 30 |
| 6 | 8 | pGX1429 | 10 | 30 |
| 7 | 8 | pGX1429 | 20 | 30 |
| 8 | 8 | pGX1429 | 30 | 30 |
| 9 | 8 | pGX1429 | 50 | 30 |

The mice in the immunized groups were vaccinated with the doses indicated of pGX0001, pGX1428, or pGX1429 according to SOP R20-003147 CELLECTRA® 3P Mouse Treatment. Briefly, plasmids were formulated in sterile water for injection (VetOne) such that the indicated dose amount was delivered by intramuscular injection into the tibialis anterior muscle in a 30 µL injection volume. Each intramuscular injection was immediately followed by electroporation (EP) using the CELLECTRA® 2000 Adaptive Constant Current Electroporation Device with a 3P array (Inovio Pharmaceuticals). The device was configured to deliver two 0.1 Amp pulses of 52 ms pulse width, spaced apart by a 1 second delay. The mice received 3 immunizations, 3 weeks apart. Mice were sacrificed one week after the last immunization and spleens harvested for cellular immune readouts. No other tissue was collected.

Splenic Lymphocyte Isolation

Splenocytes were aseptically isolated and placed in 5 mL of R10 media (Rosewell Park Memorial Institute medium 1640 supplemented with 10% fetal bovine serum and 1% antibiotic-antimycotic). Splenocytes were isolated by mechanical disruption of the spleen using a Stomacher machine (Seward Laboratory Systems Inc.), and the resulting product was filtered using a 40-µm cell strainer (BD Falcon). The resulting product was centrifuged and the pellet was treated for 5 min with ACK lysis buffer (Lonza) for lysis of RBCs. The splenocytes were then centrifuged, washed in PBS, and then resuspended in R10 media and immediately used for further analysis.

IFNγ ELISpot

Mouse IFNγ ELISpot assay was performed using a kit from MabTech (MabTech, #3321-4APW-10) to evaluate antigen-specific cellular responses. Briefly, 96 well plates pre-coated with anti-mouse IFNγ antibody (mAb AN18) were washed in PBS and blocked for 2 hours at room temperature with complete culture medium media (RPMI 1640 supplemented with 10% FBS and antibiotics). Splenic lymphocytes were re-suspended in R10 media (and then added in triplicates at an input cell number of 2×105 cells per well. A set of peptides was synthesized (GenScript), each containing 15 amino acid residues overlapping by 11 amino acids representing the entire synthetic consensus Survivin antigen 1 and synthetic consensus Survivin antigen 1T3 protein sequences. These sets of peptides were resuspended in DMSO (Sigma) and pooled at a concentration of ~2 µg/ml peptide into two peptide pools. One peptide pool contained the peptides corresponding to the synthetic consensus Survivin antigen 1 antigen protein and the second peptide pool contained the peptides corresponding the synthetic consensus Survivin antigen 1T3 antigen protein. Concavalin A (Sigma) at 5 g/ml was used as a positive control and complete culture medium was used as a negative control. Plates were incubated for 18 hours at 37° C., in a 5% $CO_2$ atmosphere incubator. Then, a biotinylated anti-mouse IFNγ detection antibody (MabTech mAb R4-6A2) was added, and plates were incubated for 2 hours at room temperature. The plates were washed, and Streptavidin-ALP (MabTech) was added and plates incubated for 1 hour at room temperature. Spot detection was completed using the BCIP/NBT substrate according to the kit manufacturer's instructions (MabTech). The spots on the plates were counted using an automated ELISPOT reader (Cellular Technology). The average number of Spot Forming Units (SFU) was adjusted to $1 \times 10^6$ splenocytes for data display.

In FIGS. 7A-7H, antigen specific responses by IFNγ ELISpot are reported as the number of IFNγ spot forming unit (SFU) per $1 \times 10^6$ splenocytes greater than the SFU in the media only control.

Flow Cytometry

Figure 8:
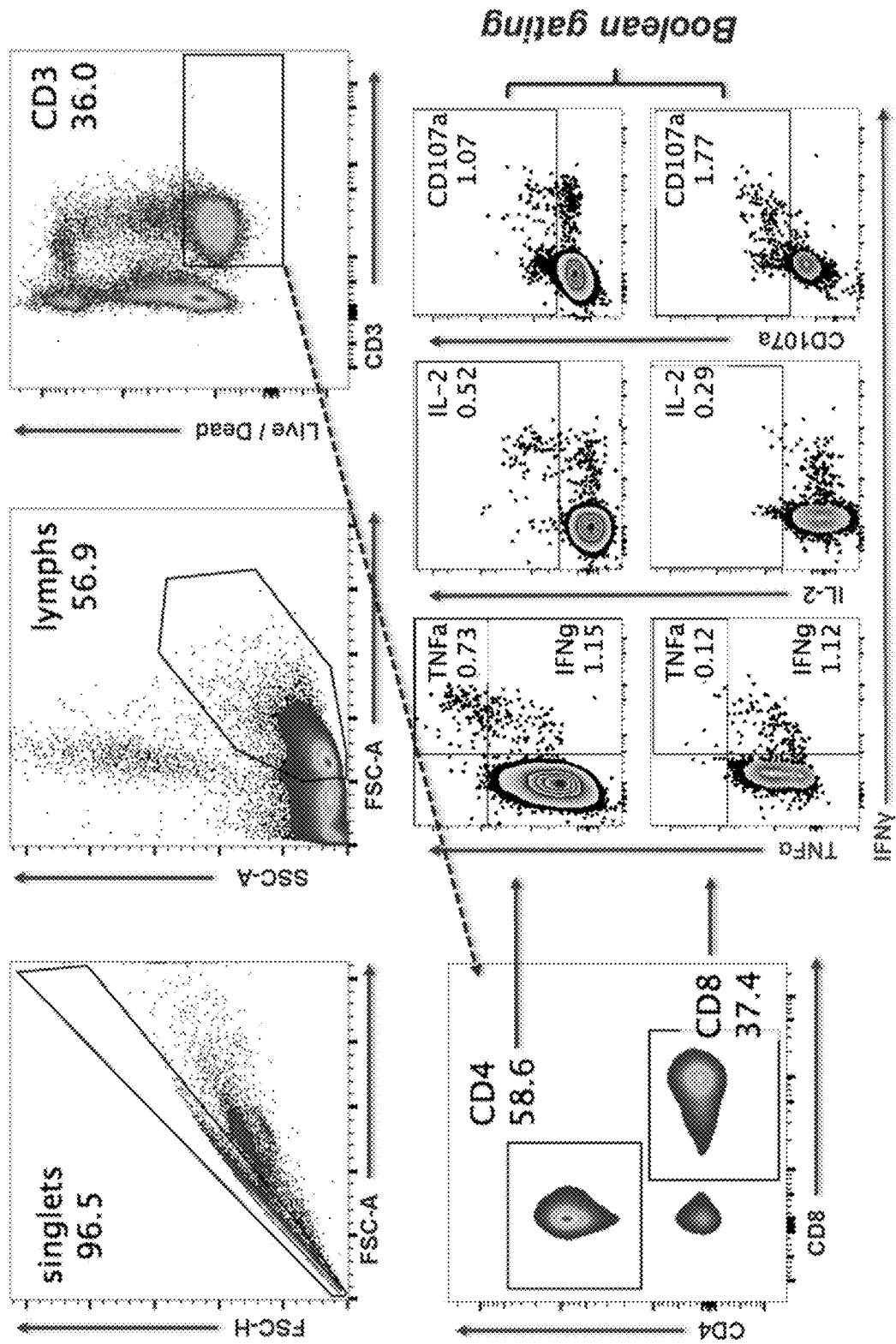
FIG. 8 shows the flow cytometry gating strategy.

Cellular immune responses induced by synthetic consensus Survivin antigen 1 and synthetic consensus Survivin antigen 1T3 were further characterized by flow cytometry. Briefly, $2 \times 10^6$ splenocytes from vaccinated and naïve mice were immediately stimulated following isolation with the synthetic consensus Survivin antigen 1 and Survivin 1T3 peptides, as appropriate for each group, for 6 hours in the presence of Brefeldin A (BD Biosciences), Monensin (BD Biosciences), and FITC anti-mouse CD107a antibody (BD Biosciences, clone 1D4B). After stimulation with peptides, splenocytes were spun down and resuspended in 20 µL per well of mouse BD Fc Block (BD Biosciences) solution. The Fc Block is used at an initial dilution of 1:40 in PBS and incubated at 4° C. for 5 minutes. After incubation, the remaining extracellular antibodies (in PBS) are added at 30 µL per well and allowed to incubate at 4° C. for 30 minutes. Upon addition of the extracellular stain, the final volume in each well is 50 µL, consisting of Fc Block at a final dilution of 1:100 and the extracellular antibodies at their appropriate working dilutions. Cells were then stained with viability dye (Vivid V450, Thermo-Fisher) and the following extracellular antibodies: PerCP-Cy5.5 anti-mouse CD4 (BD Biosciences, clone RM4-5) and APC anti-mouse CD8a (BD Biosciences, clone 63-6.7). Cell were fixed and permeabilized (BD Biosciences, #554714) for 20 minutes at 4° C. Intracellular staining was subsequently completed with the following antibodies: APC-Cy7 anti-mouse CD3e (BD Biosciences, clone 145-2C11) BV605 anti-mouse IFNγ BD Biosciences, clone XMG1.2), APC-R700 anti-mouse IL-2 (BD Biosciences, clone JEs6-5H4), and PE anti-mouse TNF-α (BD Biosciences, clone MP6-XT22). ICS data was collected on 10-color FACS CANTO (BD Biosciences) and analysis completed using FlowJo software. The flow cytometry gating strategy is shown in FIG. 8.

For a cell to be called antigen specific by flow cytometry, the frequency of the reported parameter must exceed that of the media-only control. For a cell to be identified as producing antigen specific CD107a, the cell must also be identified as positive for antigen specific production of IFNγ, and/or IL-2 and/or TNFα as identified by Boolean gating.

Statistical Analysis

Statistical analysis was completed using IBM SPSS Statistics 22 (IBM Corporation). Analysis between groups was performed using an ANOVA with post-hoc Tukey's Honest Significant Difference (HSD) to adjust for multiple comparisons. Homogeneity of variance was confirmed using the F statistic prior to multiple comparisons. For all statistical analysis, a p-value of 0.050 was considered significant.

Results

Expression of the Synthetic Consensus Survivin Antigen Proteins

Two constructs were designed to target human Survivin, synthetic consensus Survivin antigen 1 (pGX1428) and synthetic consensus Survivin antigen 1T3 (pGX1429). Expression of the synthetic consensus Survivin antigen 1 and synthetic consensus Survivin antigen 1T3 antigen proteins by pGX1428 and pGX1429, respectively, was confirmed by western blotting. Briefly, human rhabdomyosarcoma (RD) cells were transfected with the pGX1428, pGX1429 or pGX0001 (empty vector, negative control) plasmids. Cell lysates were probed for expression of the synthetic consensus Survivin antigen proteins with an anti-human Survivin antibody (BIRC5). Protein bands of the expected molecular weights for synthetic consensus Survivin antigen 1 (17.5 kD) and synthetic consensus Survivin antigen 1T3 (25.3 kD) were detected (FIG. 6). A faint band was detected in in the negative control (pGX0001) that is most likely due to low level endogenous Survivin protein expression in the RD cell line. Anti-β-actin bands were detected of similar intensities indicating equal amounts of protein were loaded in each lane. In summary, pGX1428 and pGX1429 were found to express their respective antigen proteins.

Immunogenicity of the Synthetic Consensus Survivin Antigen Vaccine Constructs IFNγ ELISpot Immunogenicity of the two synthetic consensus Survivin antigen constructs was evaluated at four dose amounts (10 µg, 20 µg, 30 µg, and 50 µg) by IFNγ ELISpot and flow cytometry (n=8/group). Mice were immunized with the empty vector backbone (pGX0001) as a negative control (n=4/group). Vaccination with synthetic consensus Survivin antigen 1 resulted in significant IFNγ responses compared to negative control vaccinated mice. However, there was minimal evidence for a dose dependent increase in IFNγ production induced by synthetic consensus Survivin antigen 1 (FIG. 7A) suggesting the maximal response was achieved at the lowest dose. Specifically, synthetic consensus Survivin antigen 1 IFNγ SFU were 1,082±574, 1,186±747, 1,135±647, and 848±350 at the 10 µg, 20 µg, 30 µg, and 50 µg, respectively. Synthetic consensus Survivin antigen 1 IFNγ responses were significantly greater than naïve (2±3) at the 10 µg (p=0.031), 20 µg (p=0.015), and 30 µg (p=0.021) doses of pGX1428, but not at the 50 µg dose (p=0.134). Vaccination with synthetic consensus Survivin antigen 1T3 resulted in significant IFNγ responses with some evidence for a dose-dependent increase with increasing dose levels (FIG. 7D). Survivin 1T3 IFNγ SFU were 516±156, 812±534, 1,016±654, and 818±339 at the 10 µg, 20 µg, 30 µg, and 50 µg, respectively. Synthetic consensus Survivin antigen 1T3 IFNγ responses were significantly greater than naïve (5±6) at the 20 µg (p=0.039), 30 µg (p=0.006), and 50 µg (p=0.037) doses of pGX1429, but not at the 10 µg dose (p=0.337). IFNγ responses are summarized in Table 5.

TABLE 5

IFN-gamma responses induced by synthetic consensus Survivin antigen 1 and synthetic consensus Survivin antigen 1T3.

| | Synthetic consensus Survivin antigen 1 HL,1 (pGX1428) | | | Synthetic consensus Survivin antigen 1T3 (pGX1429) | | | |
|---|---|---|---|---|---|---|---|
| Construct | Dose amount | Mean SFU ± Std. Dev. | p-value | Construct | Dose amount | Mean SFU ± Std. Dev. | p-value |
| pGX0001 | 30 μg | 2 ± 3 | n/a | pGX0001 | 30 μg | 5 ± 6 | n/a |
| pGX1428 | 10 μg | 1,082 ± 574 | p = 0.031 | pGX1429 | 10 μg | 516 ± 156 | p = 0.337 |
| | 20 μg | 1,186 ± 747 | p = 0.015 | | 20 μg | 812 ± 534 | p = 0.039 |
| | 30 μg | 1,135 ± 647 | p = 0.021 | | 30 μg | 1,016 ± 654 | p = 0.006 |
| | 50 μg | 848 ± 350 | p = 0.134 | | 50 μg | 818 ± 339 | p = 0.037 | p-values reported are relative to naïve (pGX0001 immunized mice)

Flow Cytometry

Figure 7G:
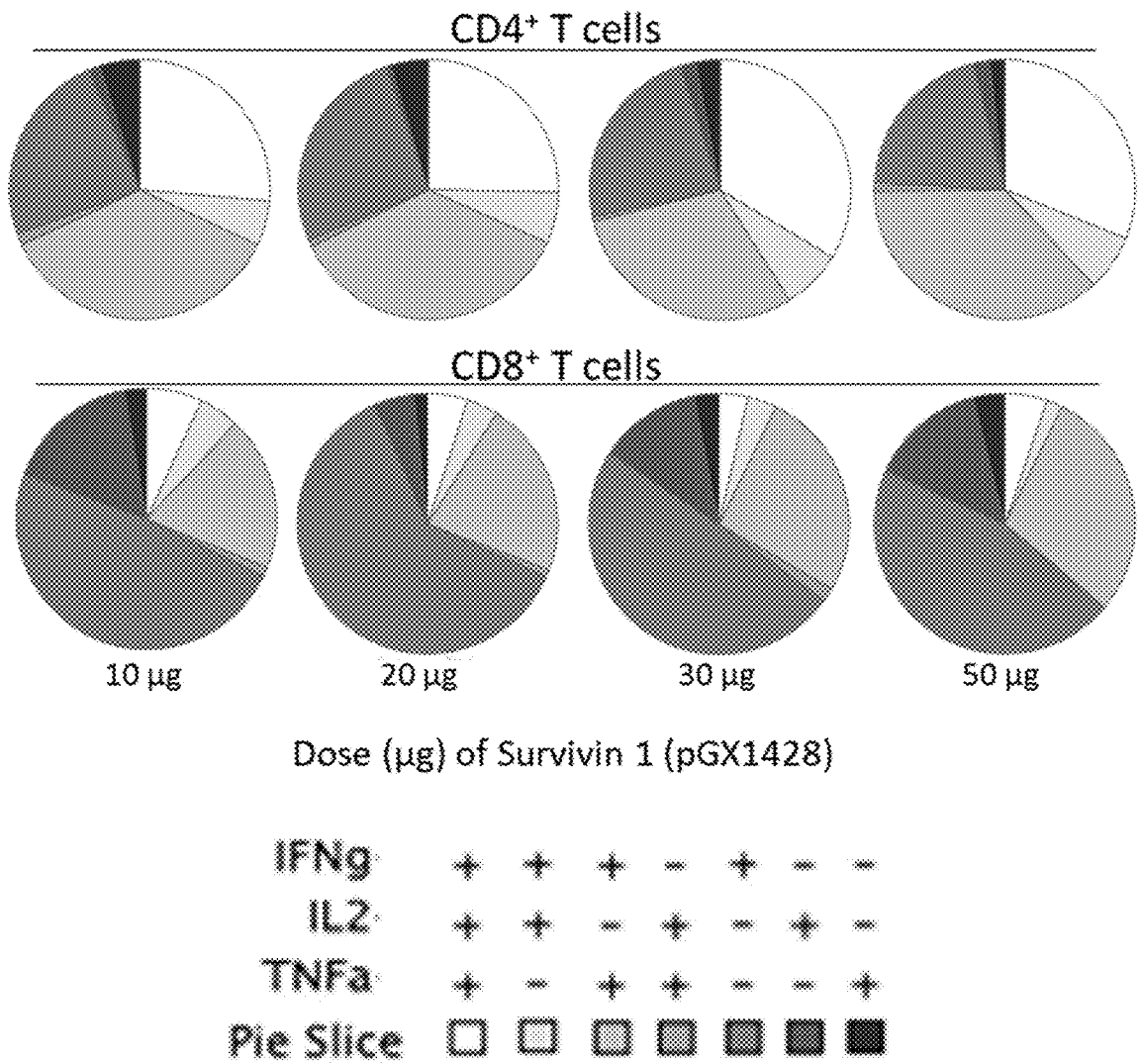
Figure 7H:
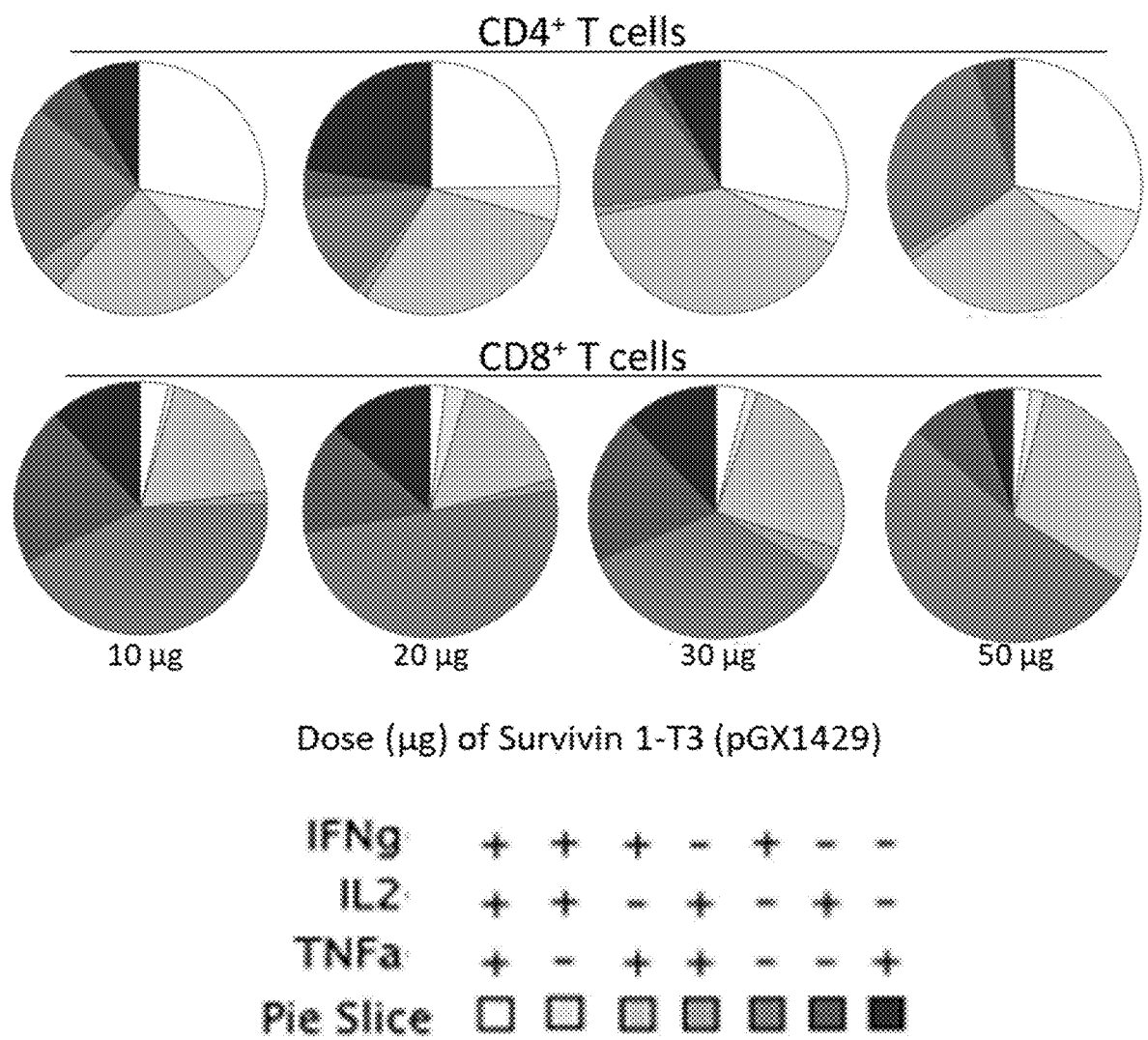
Figure 9:
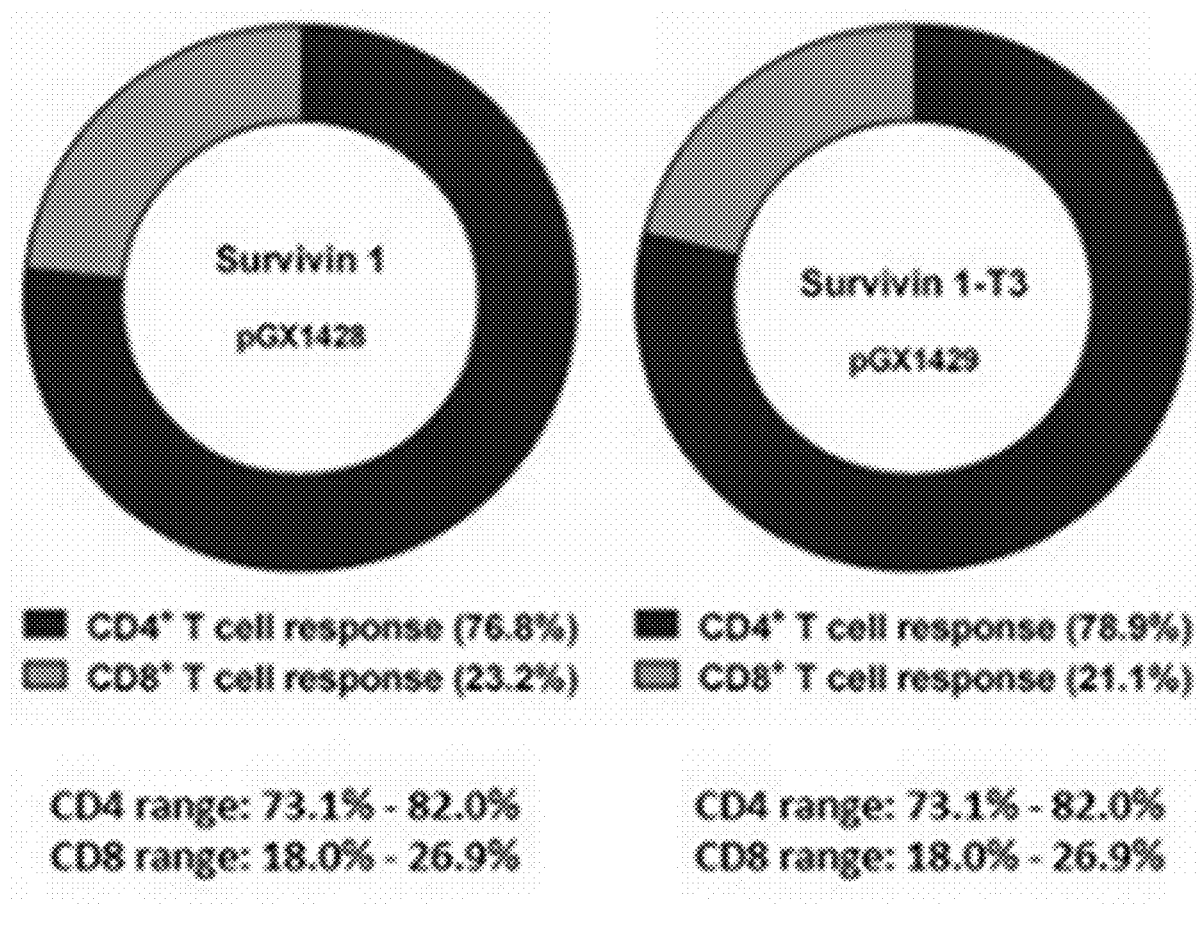
FIG. 9 shows relative frequency of CD4+ and CD8+ T cells. Cellular immune responses induced by pGX1428 and pGX1429 were predominantly in the CD4+ T cell compartment relative to the CD8+ T cell compartment.

Synthetic consensus Survivin antigen 1 and synthetic consensus Survivin antigen 1T3 both elicited more robust responses in the CD4+ T cell compartment, relative to the responses in the CD8+ T cell compartment (FIG. 9). Synthetic consensus Survivin antigen 1 induced frequencies of antigen specific CD4+ T cell responses that were significantly more robust than naïve (0.03%±0.05%) in the 20 μg (1.08%±0.65%) (p=0.024) and 50 ag (1.21% 0.73%) (p=0.009) dose amount groups, but not in the 10 ag (0.86%±0.31%) (p=0.105) or 30 ag (0.82%±0.46%) (p=0.134) dose amount groups (FIG. 7B). Synthetic consensus Survivin antigen 1T3 induced antigen specific CD4+ T cell responses that were significantly more robust than naïve (0.05%±0.05%) in the 20 μg (1.02%±0.59%) (p=0.010), 30 μg (1.08%±0.47%) (p=0.006), and 50 μg (1.13%±0.44%) (p=0.004) dose amount groups, but not in the 10 μg (0.62%±0.35%) (p=0.248) dose amount group (FIG. 7E). The cytokine profile of synthetic consensus Survivin antigen specific CD4+ T cells was similar for both constructs, across dose amount groups, and was comprised mainly of IFNγ+IL-2+TNFα+, IFNγ+IL-2-TNFα+, or IFNγ+IL-2-TNFα-cells (FIG. 7G, FIG. 7H). The frequency of antigen specific CD4+ T cells is further detailed in Table 6.

There was not a significant difference in the frequency of antigen specific CD8+ T cells induced by synthetic consensus Survivin antigen 1 (p=0.117) (FIG. 7C). Survivin 1T3 did induce a significantly greater frequency of antigen specific CD8+ T cells between groups dose amount groups (p=0.043). The frequency of antigen specific CD8+T responses in the groups immunized with 10 μg (0.15%±0.09%) (p=0.919), 20 μg (0.27%±0.21%) (p=0.274), or 30 μg (0.25%±0.14%) (p=0.377) of pGX1429 did not approach statistical significance compared to naïve (0.07%±0.01%). The frequency of Survivin 1T3 specific CD8+ T cells approached statistical significance (0.36%±0.21%) (p=0.051) in the group immunized with 50 μg of pGX1429 (FIG. 7F). Both synthetic consensus Survivin antigen 1 and synthetic consensus Survivin antigen 1T3 induced CD8+ T cell responses similar in magnitude and phenotype. Antigen specific CD8+ T cells were primarily IFNγ+IL-2-TNFα-, IFNγ+IL-2-TNFα+(FIG. 7G, FIG. 7H). The frequency of antigen specific CD8+ T cells is further detailed in Table 7.

TABLE 6

CD4+ T cell responses induced by synthetic consensus Survivin antigen 1 and synthetic consensus Survivin antigen 1T3.

| | Synthetic consensus Survivin antigen 1 | | | Synthetic consensus Survivin antigen 1T3 | | | |
|---|---|---|---|---|---|---|---|
| Construct | Dose amount | % CD4+ ± Std. Dev. | p-value | Construct | Dose amount | % CD4+ ± Std. Dev. | p-value |
| pGX0001 | 30 μg | 0.03 ± 0.05 | n/a | pGX0001 | 30 μg | 0.05 ± 0.05 | n/a |
| pGX1428 | 10 μg | 0.86 ± 0.31 | p = 0.105 | pGX1429 | 10 μg | 0.62 ± 0.35 | p = 0.248 |
| | 20 μg | 1.08 ± 0.65 | p = 0.024 | | 20 μg | 1.02 ± 0.59 | p = 0.010 |
| | 30 μg | 0.82 ± 0.46 | p = 0.134 | | 30 μg | 1.08 ± 0.47 | p = 0.006 |
| | 50 μg | 1.21 ± 0.73 | p = 0.009 | | 50 μg | 1.13 ± 0.44 | p = 0.004 | p-values reported are relative to naïve (pGX0001 immunized mice)

TABLE 7

CD8+ T cell responses induced by synthetic consensus Survivin antigen 1 and synthetic consensus Survivin antigen 1T3

| | Synthetic consensus Survivin antigen 1 | | | | Synthetic consensus Survivin antigen 1T3 | | |
|---|---|---|---|---|---|---|---|
| Construct | Dose amount | % CD8+ ± Std. Dev. | p-value | Construct | Dose amount | % CD8+ ± Std. Dev. | p-value |
| pGX0001 | 30 µg | 0.03 ± 0.01 | n/a | pGX0001 | 30 µg | 0.07 ± 0.01 | n/a |
| pGX1428 | 10 µg | 0.21 ± 0.11 | between | pGX1429 | 10 µg | 0.15 ± 0.09 | p = 0.919 |
| | 20 µg | 0.35 ± 0.31 | groups | | 20 µg | 0.27 ± 0.21 | p = 0.274 |
| | 30 µg | 0.25 ± 0.12 | p = 0.117 | | 30 µg | 0.25 ± 0.14 | p = 0.377 |
| | 50 µg | 0.24 ± 0.15 | | | 50 µg | 0.36 ± 0.21 | p = 0.051 | p-values reported are relative to naïve (pGX0001 immunized mice)

Figure 10A:
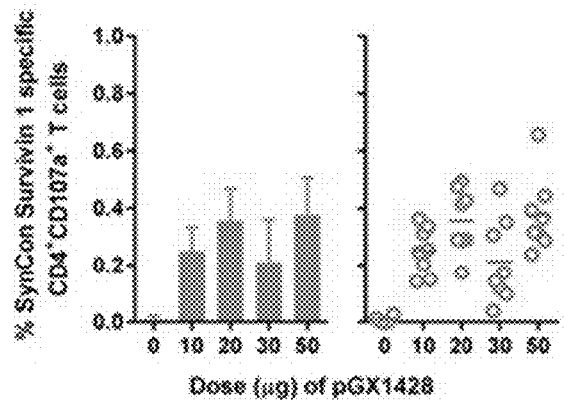
FIGS. 10A to 10F show cytolytic potential of Survivin specific T cells. Cytolytic potential of antigen specific T cells induced by Survivin 1 and Survivin 1T3.
Figure 10B:
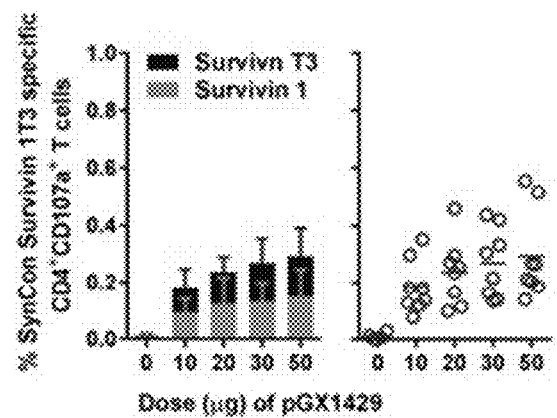

Approximately 25% of the cytokine positive CD4+ T cells induced by synthetic consensus Survivin antigen 1 (FIG. 10A) and synthetic consensus Survivin antigen 1T3 (FIG. 10B) were also positive for CD107a, indicating some potential for CD4+ T cell mediated cytolytic function. All dose amounts of synthetic consensus Survivin antigen 1 induced a frequency of CD4+CD107a+ T cells significantly greater than naïve (0.01%±0.01%). Specifically, the frequency of antigen specific CD4+CD107a+ T cells was 0.25%±0.08%, 0.36%±0.11%, 0.21%±0.15%, and 0.38%±0.13% in the 10 µg (p=0.013), 20 µg (p<0.001), g (p=0.050), and 50 µg (p<0.001) dose amount groups, respectively (FIG. 10A). Synthetic consensus Survivin antigen 1T3 induced a frequency of CD4+CD107a+ T cells significantly greater than naïve (0.01±0.01) in all groups except the 10 µg dose amount group (0.18%±0.0.09%) (p=0.147). The frequency of antigen specific CD4+CD107a+ T cells was 0.24% 0.12%, 0.27%±0.12%, and 0.29%±0.16% in the 20 µg (p=0.030), 30 µg (p=0.010), and 50 µg (p=0.004) dose amount groups, respectively (FIG. 10B). The frequency of antigen specific CD4+ T cells with cytolytic potential is further detailed in Table 8.

Figure 10C:
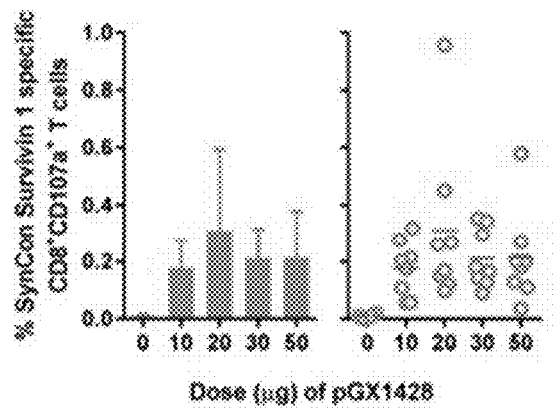
Figure 10D:
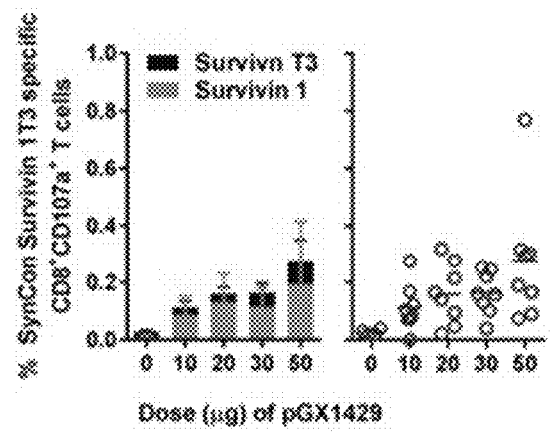
Figure 10E:
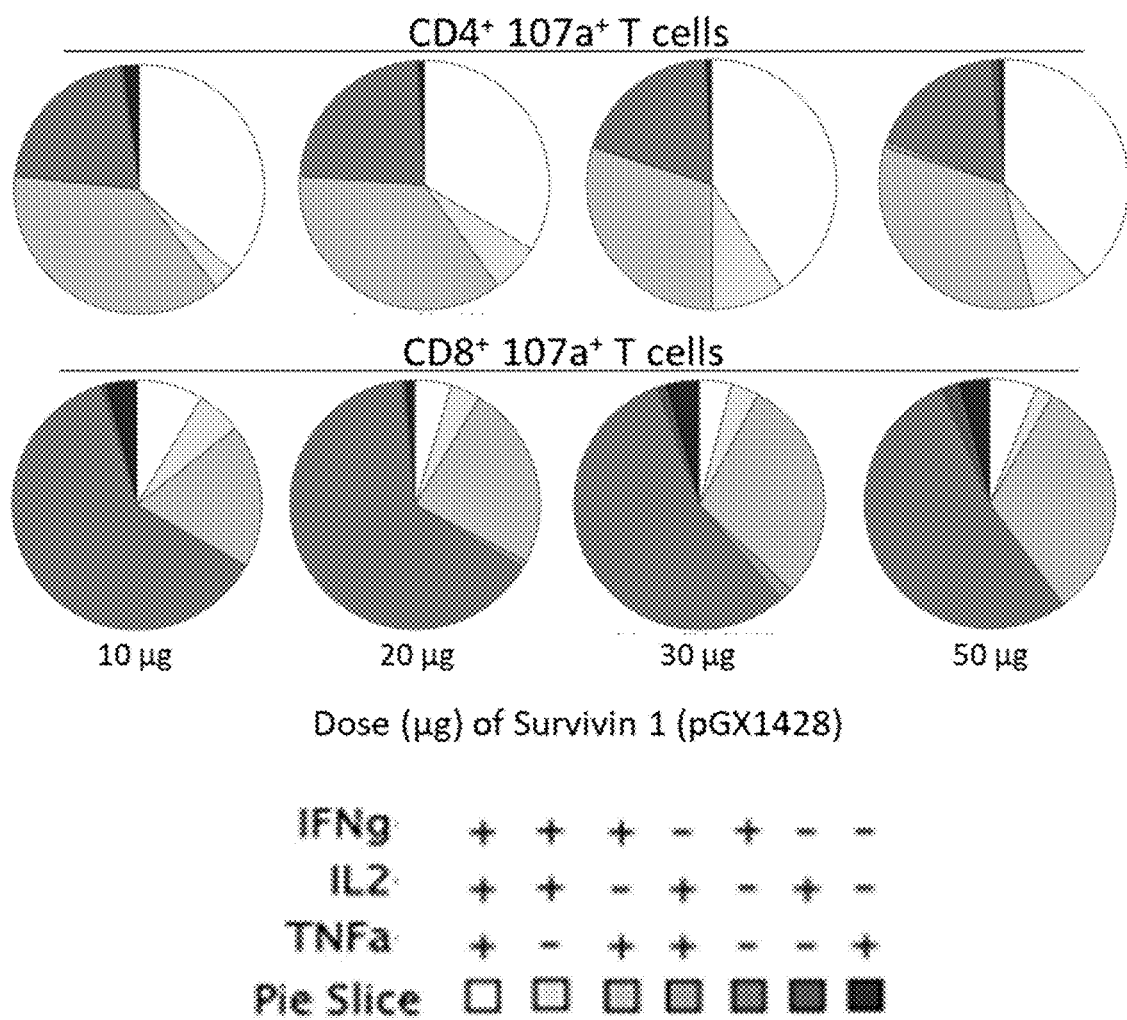
Figure 10F:
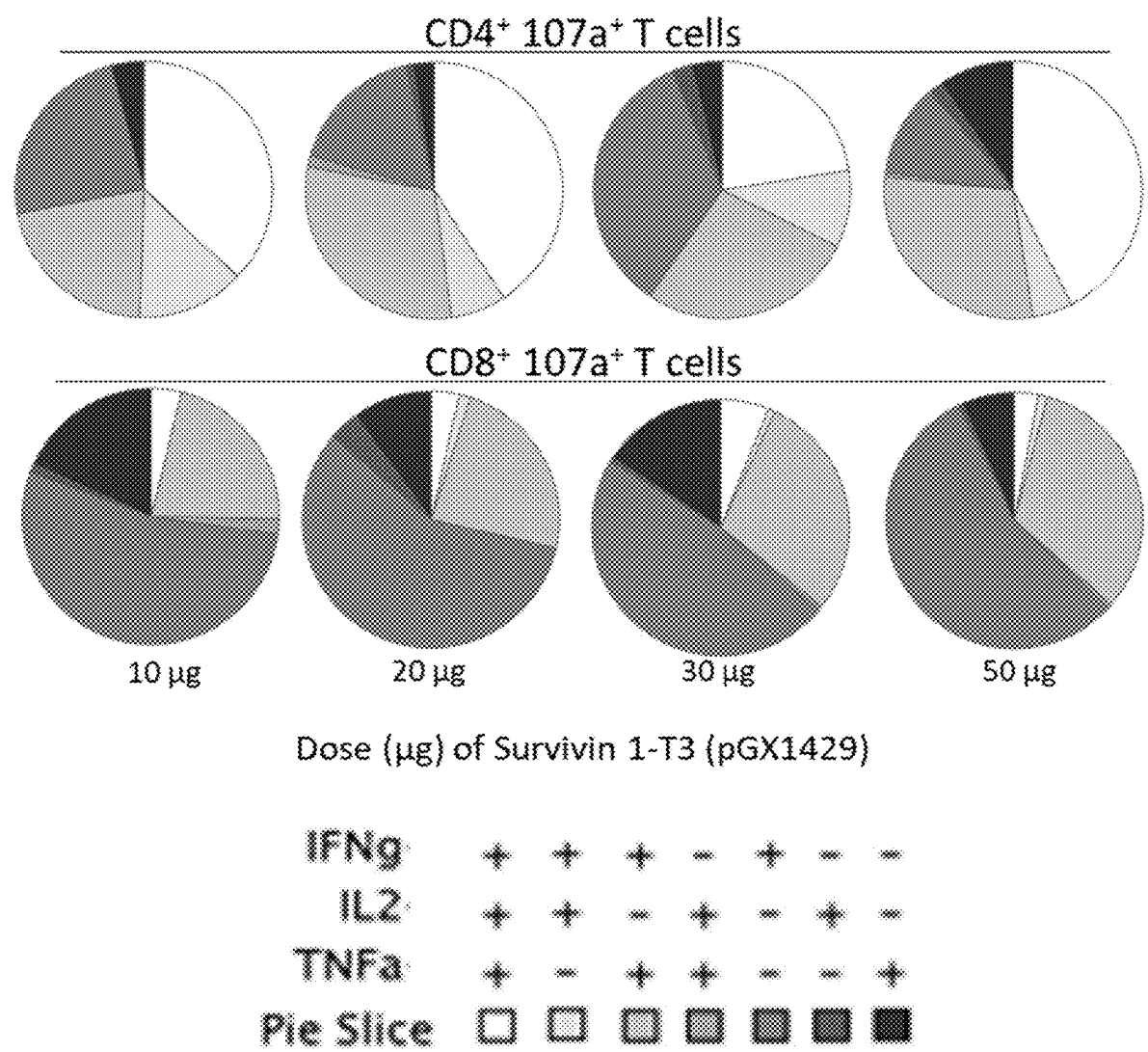

Similar to the magnitude of antigen specific CD8+ T cells, synthetic consensus Survivin antigen 1 did not induced a significant change in the frequency of CD8+CD107a+ T cells among all groups (p=0.101) (FIG. 10C). Synthetic consensus Survivin antigen 1T3 did induce a significant change in the frequency of CD8+CD107a+ T cells between all dose amount groups (p=0.034) (FIG. 10D). The frequency of antigen specific CD8+CD107a+ T cells significantly increased above naïve (0.03±0.01) in the group immunized with 50 µg of pGX1429 (0.28%±0.22%) (p=0.026), but not in the groups immunized with 10 µg (0.11% 0.08%) (p=0.813), 20 µg (0.16%±0.11%) (p=0.450), 30 µg (0.16%±0.07%) (p=0.424) of synthetic consensus Survivin antigen 1T3. The cytokine profile of synthetic consensus Survivin antigen specific CD8+CD107a+ T cells was similar for both constructs, across dose amount groups, and was comprised mainly of IFNγ+IL-2-TNFα+, IFNγ+IL-2-TNFα-cells (FIG. 10E, FIG. 10F). The frequency of antigen specific CD8+ T cells with cytolytic potential is further detailed in Table 9.

TABLE 8

Cytolytic potential of antigen specific CD4+ T cells induced by synthetic consensus Survivin antigen 1 and synthetic consensus Survivin antigen 1T3

| | Synthetic consensus Survivin antigen 1 | | | | Synthetic consensus Survivin antigen 1T3 | | |
|---|---|---|---|---|---|---|---|
| Construct | Dose amount | % CD4+CD107a+ ± Std. Dev. | p-value | Construct | Dose amount | % CD4+CD107a+ ± Std. Dev. | p-value |
| pGX0001 | 30 µg | 0.01 ± 0.01 | n/a | pGX0001 | 30 µg | 0.01 ± 0.01 | n/a |
| pGX1428 | 10 µg | 0.25 ± 0.08 | p = 0.013 | pGX1429 | 10 µg | 0.18 ± .09 | p = 0.147 |
| | 20 µg | 0.36 ± 0.11 | p < 0.001 | | 20 µg | 0.24 ± 0.12 | p = 0.030 |
| | 30 µg | 0.21 ± 0.15 | p = 0.050 | | 30 µg | 0.27 ± 0.12 | p = 0.010 |
| | 50 µg | 0.38 ± 0.13 | p < 0.001 | | 50 µg | 0.29 ± 0.16 | p = 0.004 | p-values reported are relative to naïve (pGX0001 immunized mice)

TABLE 9

Cytolytic potential of antigen specific CD8+ T cells induced by synthetic consensus
Survivin antigen 1 and synthetic consensus Survivin antigen 1T3

| | Synthetic consensus Survivin antigen 1 | | | Synthetic consensus Survivin antigen 1T3 | | | |
| --- | --- | --- | --- | --- | --- | --- | --- |
| Construct | Dose amount | % CD8+CD107a+ ± Std. Dev. | p-value | Dose Construct | amount | % CD8+CD107a+ ± Std. Dev. | p-value |
| pGX0001 | 30 μg | 0.01 ± 0.01 | n/a | pGX0001 | 30 μg | 0.03 ± 0.01 | n/a |
| pGX1428 | 10 μg | 0.18 ± 0.10 | between | pGX1429 | 10 μg | 0.11 ± 0.08 | p = 0.813 |
| | 20 μg | 0.31 ± 0.28 | groups | | 20 μg | 0.16 ± 0.11 | p = 0.450 |
| | 30 μg | 0.21 ± 0.10 | p = 0.101 | | 30 μg | 0.16 ± 0.07 | p = 0.424 |
| | 50 μg | 0.21 ± 0.16 | | | 50 μg | 0.28 ± 0.22 | p = 0.026 | p-values reported are relative to naïve (pGX0001 immunized mice)

Breadth of IFNγ Responses Induced by the Synthetic Consensus Survivin Antigen Constructs The breadth of IFNγ responses to Survivin induced by pGX1428 and pGX1429 was examined by epitope mapping using a peptide matrix pool approach (FIG. 11A-11D). Pooled splenic lymphocytes from mice immunized with the highest dose amount of pGX1428 (n=8) (FIG. 11A) or pGX1429 (n=8) (FIG. 11B) were examined.

The following synthetic consensus Survivin antigen 1 epitopes were present in both the pGX1428 and pGX1429:

```
(matrix pools 1, 2, 3, 4, and 7)
                             (SEQ ID NO: 5)
LPPAWQLFLKDHRISTFKN (matrix pools 1, 2, 3, 4 and 11)
                             (SEQ ID NO: 6)
LKLDRERAKNKIAKETNNK
```

Synthetic Consensus Survivin Antigen T3 Epitopes Present in pGX1429:

```
(matrix pools 3, 4 and 7)
                             (SEQ ID NO: 7)
EWLHHFQGLFP
```

While the total magnitude of cellular immune responses induced by synthetic consensus Survivin antigen 1 and synthetic consensus Survivin antigen 1T3 was similar, responses induced by synthetic consensus Survivin antigen 1T3 (pGX1429) against the synthetic consensus Survivin antigen 1 (pGX1428) region of the synthetic consensus Survivin antigen 1T3 were approximately half the magnitude of those induced by the synthetic consensus Survivin antigen 1 construct (pGX1428). Epitope mapping by IFNγ ELISpot using a matrix approach revealed that both synthetic consensus Survivin antigen constructs generate responses to the same epitopes in the synthetic consensus Survivin antigen 1 antigen, but responses driven by synthetic consensus Survivin antigen 1T3 against these epitopes are lower in magnitude. It was also determined that there is a unique epitope in the T3 region of the synthetic consensus Survivin antigen 1T3 antigen.

While the total magnitude of cellular immune responses induced by synthetic consensus Survivin antigen 1 (pGX1428) and synthetic consensus Survivin antigen 1T3 (pGX1429) were similar, responses induced by synthetic consensus Survivin antigen 1T3 (pGX1429) against the synthetic consensus Survivin antigen 1 region of the synthetic consensus Survivin antigen 1T3 antigen were approximately half the magnitude of those induced by the synthetic consensus Survivin antigen 1 construct (pGX1428). Epitope mapping by IFNγ ELISpot using a matrix approach revealed that both synthetic consensus Survivin antigen constructs generate responses to the same epitopes as the synthetic consensus Survivin antigen 1 antigen, but responses driven by synthetic consensus Survivin antigen 1T3 against these epitopes are lower in magnitude. It was also determined that there is a unique epitope in the T3 region of the synthetic consensus Survivin antigen 1T3 antigen using this approach. Synthetic consensus Survivin antigen 1T3 also significantly increased the frequency of antigen specific CD8+ and CD8+CD107a+ T cells, compared to naïve, while synthetic consensus Survivin antigen 1 did not significantly increase antigen specific CD8+ T cells in mice. Synthetic consensus Survivin antigen 1T3 (pGX1429) was selected to move forward into a monovalent non-human primate study based on its potential to further enhance the breadth of cellular immune responses to Survivin as compared to pGX1428 in mice.

Example 5—Non-Human Primate Studies Using Synthetic Consensus Survivin Antigen 1T3 (pGX1429)

Figure 12:
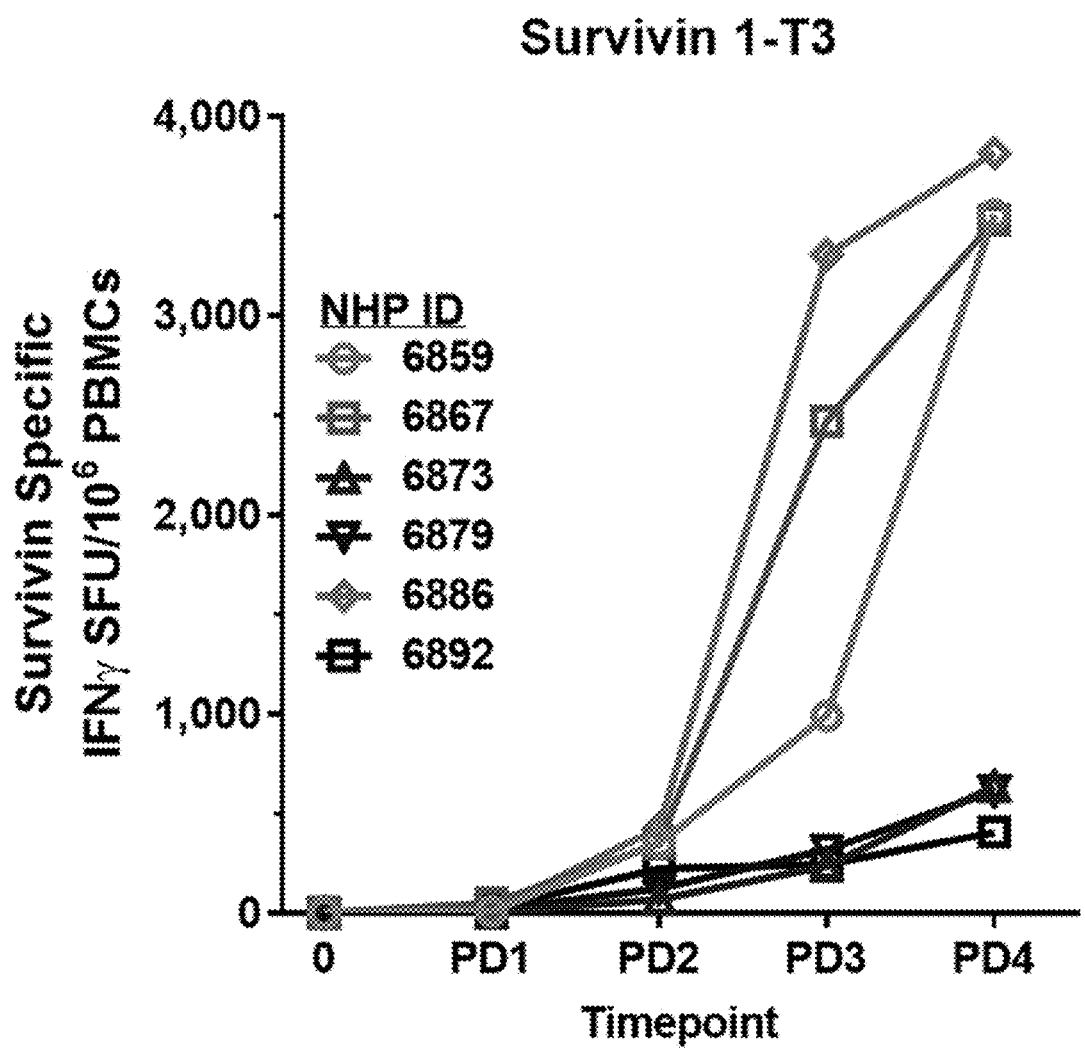
FIG. 12 shows Survivin-specific IFNγ SFU/$10^6$ PBMCs from individual non-human primates immunized using an embodiment of the disclosure comprising synthetic consensus Survivin 1T3.
Figure 13:
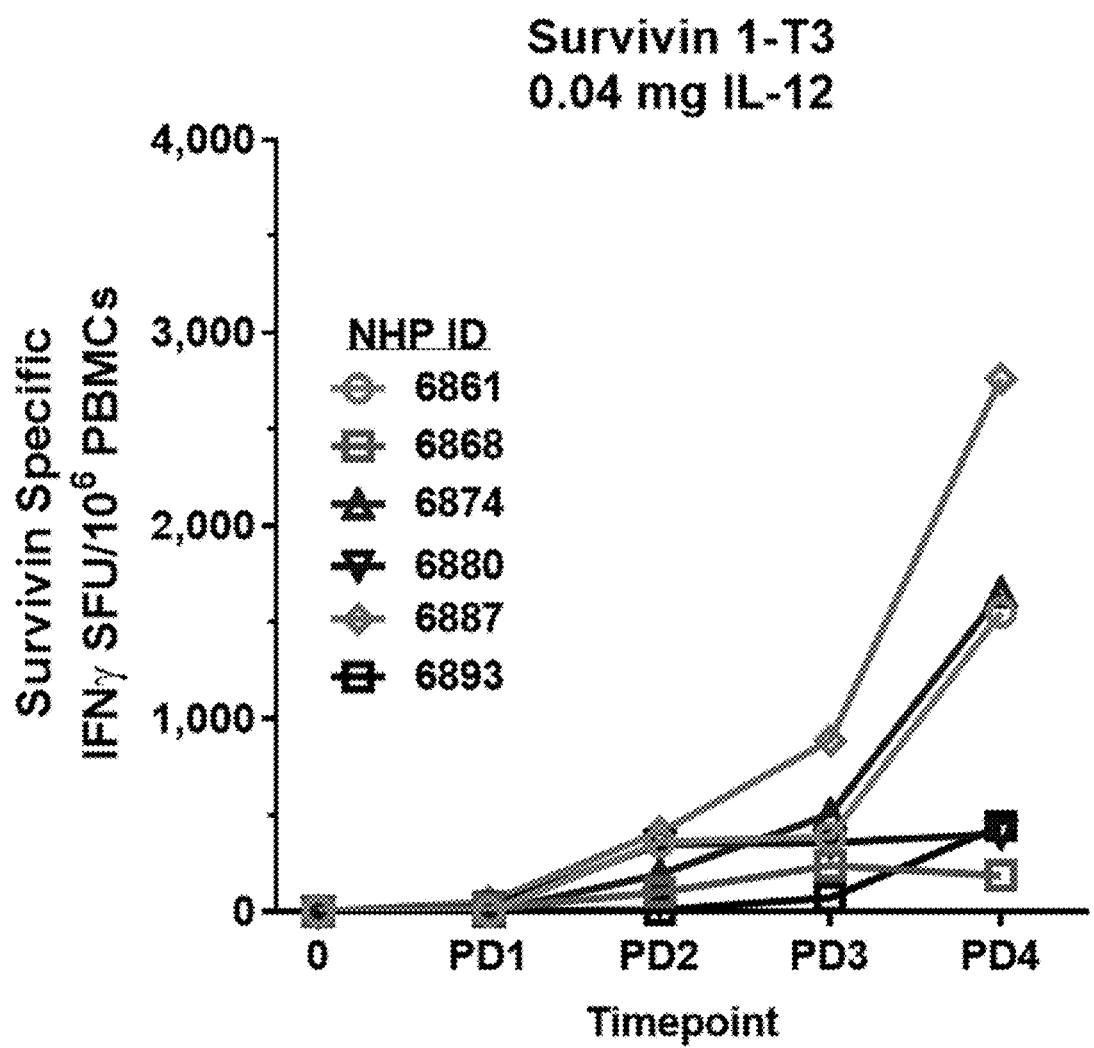
FIG. 13 shows Survivin-specific IFNγ SFU/$10^6$ PBMCs from individual non-human primates immunized using an embodiment of the disclosure comprising synthetic consensus Survivin 1T3 with a low dose of IL-12 (0.04 mg).
Figure 14:
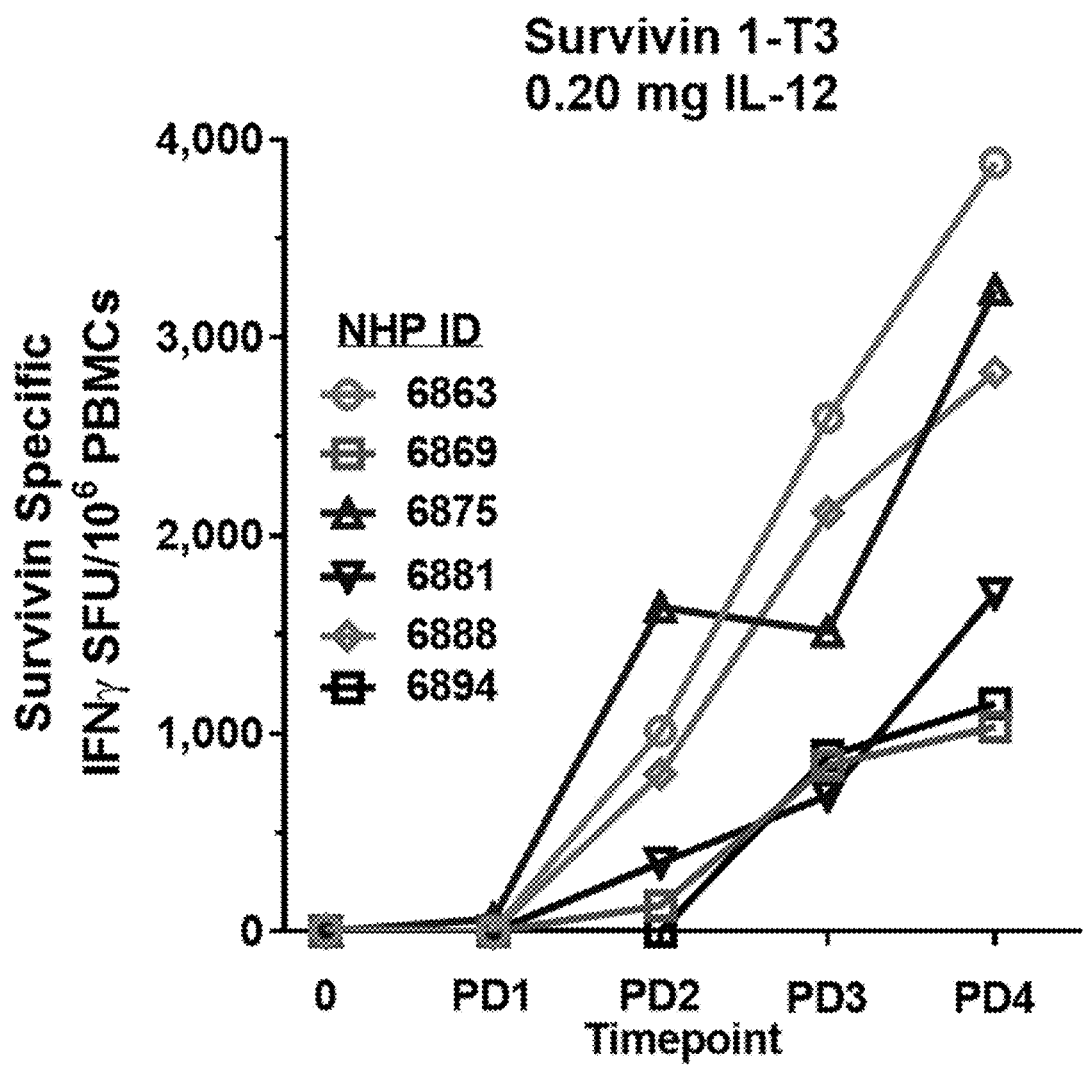
FIG. 14 shows Survivin-specific IFNγ SFU/$10^6$ PBMCs from individual non-human primates immunized using an embodiment of the disclosure comprising synthetic consensus Survivin 1T3 with a high dose of IL-12 (0.20 mg).
Figures 15A, 15B, 15C:
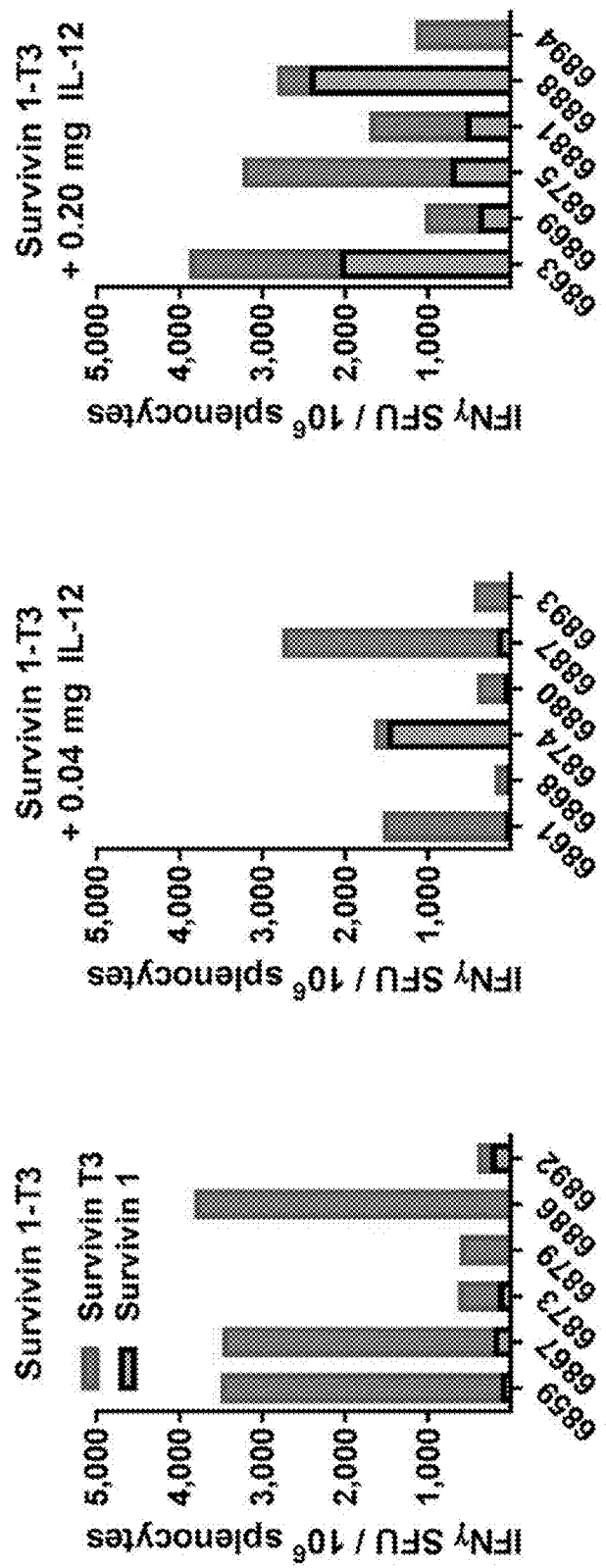
FIGS. 15A to 15C show individual animal results of the NHP study and also show a comparison between immunization with a synthetic consensus Survivin 1 construct and a synthetic consensus Survivin 1T3 construct.

To investigate the potential of Synthetic Consensus Survivin 1T3 alone and in combination with a low and high dose of IL-12, eighteen adult rhesus monkeys, each identified by a unique NHP ID number, were divided in 3 groups of 6 and immunized with pGX1429 as follows. Six animals were immunized with 3.0 mg pGX1429, six with 3.0 mg pGX1429 plus 0.04 mg of pGX6006 (opt rh IL-12) as an adjuvant, and six with 3.0 mg pGX1429 plus 0.20 mg of pGX6006 (opt rh IL-12) as an adjuvant, was formulated in SSC in 1.0 mL injection volume. Immunization injections were administered at week 0, 4, 8, and 12. All immunizations were carried out intramuscularly with CELLECTRA® 2000 5P-IM EP device in a 1 ml injection volume formulated in sterile WFI in alternating contralateral limbs according. The EP conditions were as follows: OpBlock 0070—IM, 0.5 Amp, 3 pulses, 52 msec, 0.2 sec between pulses. Survivin immunogenicity was assessed at weeks 2, 6, 10, and 14. Survivin-specific IFN-gamma responses are shown in FIGS. 12 and 13. Homology between native rhesus Survivin and pGX1429 is given in Table 10. As shown in FIGS. 13 and 14, increased Survivin-specific responses were observed in animals immunized with synthetic consensus Survivin antigen 1T3 plus 0.20 mg IL-12 as adjuvant.

PBMC Isolation

The Non-Human Primate whole blood was collected in sodium citrate cell preparation tubes (CPT CPT's BD Biosciences) containing an anticoagulant and a gel barrier. Prior to overnight shipment, whole blood is spun shortly after collection (within 2 hours) in order to separate and concentrate PMBC. Red blood cells and neutrophils pellet to the bottom of the tubes and are held in place by a gel barrier. Plasma and lymphocytes remain above the gel barrier. Each CPT can hold ~8 mL of blood and is shipped at room temperature. The spun CPT tubes were processed for PBMC isolation. After red blood cell lysis with ammonium-chloride-potassium (ACK) buffer, viable cells were counted using Invitrogen Countess™ Automated Cell Counter and resuspended in complete culture media (RPMI 1640 supplemented with 10% FBS, antibiotics, and R Mercaptoethanol). Upon completion of assays as described herein, remaining PBMCs were frozen in freezing media (10% DMSO from Sigma in 90% FBS from Seradigm) in cryovials and stored long term in liquid nitrogen.

IFNγ ELISpot

To evaluate vaccine induced antigen-specific cellular responses, a Monkey IFNγ ELISpot assay was performed at each time point on isolated PMBCs using a kit (MabTech IFNγ ELISpotPro, #3421M-2APW-10). In brief, 96 well plates pre-coated with anti-Monkey IFNγ antibody (mAb MT126L) were washed in PBS and blocked for 2 hours at room temperature with complete culture media (RPMI 1640 supplemented with 10% FBS, antibiotics, and § Mercaptoethanol). NHP PBMC were re-suspended in R10 media (and then added in triplicates at an input cell number of $2 \times 10^5$ cells per well. A set of peptides was synthesized (GenScript), each containing 15 amino acid residues overlapping by 11 amino acids representing the entire synthetic consensus protein sequences. These sets of peptides were resuspended in DMSO (Sigma) and pooled at a concentration of approximately 2 μg/mL of each respective peptide, into pools. All antigen specific pooled peptides are used at a 1:100 dilution, which results in a final dilution of 1:200 in each well when combined with PBMC. The variation in size of each antigen protein, resulted in 2 peptide pools for Survivin.

Anti-CD3 (mAb CD-2 Mabtech) and/or PMA (Sigma) with Ionomycin (Sigma) were used as a positive control. Complete R10 culture medium was used as a negative control. Plates were incubated for approximately 18 hours at 37° C., in a 5% $CO_2$ atmosphere incubator. After cell removal, and addition of an ALP conjugated anti-monkey IFNγ detection antibody (MabTech Ab 7-B6-1-ALP), the plates were incubated for 2 hours at room temperature. The sandwich immune-enzyme assay is then developed using the BCIP/NBT substrate solution according to the kit manufacturer's instructions (MabTech). A blue-black colored precipitate forms as spots to reveal each individual IFNγ producing cell. The spots are then scanned and counted by the CTL ImmunoSpot® Analyzer and Software (Cellular Technology), and quality controlled by a trained operator. The IFNγ responses are reported as Spot Forming Units (SFU) to $1 \times 10^6$ PBMC greater than the SFU in the media only control.

TABLE 10

Characteristics of synthetic consensus Survivin antigen 1T3 compared to native rhesus Survivin.

| | Region | Native rhesus |
|---|---|---|
| pGX1429 | Full-length | 95.8% (NP_001253110.1) |
| pGX1429 | Isoform 1 Region | 95.9% (NP_001253110.1) |
| pGX1429 | T3 Region | 9.4% (NP_001253110.1) |

TABLE 11

Construct, Antigen, Dose

| Construct ID | Antigen | Dose (mg) |
|---|---|---|
| pGX1429 | Synthetic Consensus Survivin 1T3 | 3 |
| pGX6006 | opt rIL-12 | 0.04 or 0.2 |

Groups 1, 2 and 3 received the following:
Group 1-3.0 mg pGX1429 (Synthetic Consensus Survivin 1T3). Formulated in SSC, 1.0 mL injection volume, IM.
Group 2-3.0 mg pGX1429 (Synthetic Consensus Survivin 1T3)+0.04 pGX6006 (opt. rIL-12). Formulated in SSC, 1.0 mL injection volume, IM.
Group 3-3.0 mg pGX1429 (Synthetic Consensus Survivin 1T3)+0.20 pGX6006 (opt. rIL-12). Formulated in SSC, 1.0 mL injection volume, IM.

All groups were immunized according to the following schedule:
Immunization 1 (Week 0)
Immunization 2 (Week 4)
Immunization 3 (Week 8)
Immunization 4 (Week 12)
Immunization 5 (Optional)

Results

Survivin specific IFNγ responses are shown in FIGS. 12-14 for Groups 1-3, respectively. The results show the response at each time point 2 weeks post dose. Overall, all groups and individual animals had an increase in response by the end of the study at 2 weeks post dose 4 compared to baseline prebleed. The addition of the higher dose of IL-12 (0.2 mg) resulted in greater and more consistent responses at each time point compared to Survivin alone or Survivin plus 0.04 mg IL-12. Higher responses as early as PD2 were also noted for Survivin plus IL-12 0.2 mg.

There were no differences in any of the physiological parameters measured due to immunization as shown in Tables 12-14. No significant differences were noted for RBCs, HCTs, neutrophils, lymphocytes, monocytes, eosinophils (results not shown). These values are within the expected ranges for animals of this species, gender, and age undergoing similar experimental procedures. Any variations from stated normal ranges are of a sporadic nature, present in only one gender, and are not related to dose levels or timing.

TABLE 12

Assessment of physiological parameters in Group 1

| | Pre-Vaccination | Post-Vaccination | | Normal |
|---|---|---|---|---|
| Group 1 | Week −2 | Week 6 | Week 14 | Range |
| WBC Count (#/$10^3$/ml) | 7.8-14.3 | 4.8-9.6 | 4.9-11.2 | 4.0-15.0 |
| Creatinine (mg/dL) | 0.4-0.8 | 0.4-0.7 | 0.4-0.8 | 0.3-1.4 |
| BUN (mg/dL) | 11-17 | 13-18 | 13-18 | 9-29 |
| ALK P (U/L) | 232-491 | 184-491 | 212-505 | 65-641 |
| AST (U/L) | 17*-24 (#6867, 6859, 6892, 6873) | 10*-24 (#6867, 6859, 6892, 6873, 6879) | 20*-36 (#6859) | 23-175 |

TABLE 12-continued

Assessment of physiological parameters in Group 1

| Group 1 | Pre-Vaccination Week −2 | Post-Vaccination Week 6 | Post-Vaccination Week 14 | Normal Range |
|---|---|---|---|---|
| ALT (U/L) | 20-40 | 17-38 | 12-31 | 18-204 |
| TBIL (mg/dL) | 0.1-0.2 | 0.1-0.2 | 0.1-0.2 | 0.1-0.6 |

Note:
Outside of normal range*

TABLE 13

Assessment of physiological parameters in Group 2

| Group 2 | Pre-Vaccination Week −2 | Post-Vaccination Week 6 | Post-Vaccination Week 14 | Normal Range |
|---|---|---|---|---|
| WBC Count (#/10$^3$/ml) | 6.3-10.8 | 5.7-8.5 | 6.2-12.1 | 4.0-15.0 |
| Creatinine (mg/dL) | 0.6-0.7 | 0.5-0.6 | 0.5-0.7 | 0.3-1.4 |
| BUN (mg/dL) | 10-19 | 12-21 | 10-23 | 9-29 |
| ALK P (U/L) | 269-508 | 279-521 | 295-455 | 65-641 |
| AST (U/L) | 15*-32 (#6868, 6874, 6880, 6887, 6893) | 12*-26 (#6874, 6868, 6861) | 21*-38 (#6893) | 23-175 |
| ALT (U/L) | 19-33 | 16*-28 (#6861) | 19-30 | 18-204 |
| TBIL (mg/dL) | 0.1-0.2 | 0.2 | 0.1-0.2 | 0.1-0.6 |

Note:
Outside of normal range*

TABLE 14

Assessment of physiological parameters in Group 3

| Group 3 | Pre-Vaccination Week −2 | Post-Vaccination Week 6 | Post-Vaccination Week 14 | Normal Range |
|---|---|---|---|---|
| WBC Count (#/10$^3$/ml) | 6.0-12.8 | 5.6-9.2 | 5.8-9.8 | 4.0-15.0 |
| Creatinine (mg/dL) | 0.5-0.7 | 0.4-0.7 | 0.5-0.7 | 0.3-1.4 |
| BUN (mg/dL) | 10-16 | 14-18 | 9-20 | 9-29 |
| ALK P (U/L) | 186-345 | 156-406 | 198-476 | 65-641 |
| AST (U/L) | 12*-47 (#6894, 6869) | 12*-68 (#6894, 6869) | 23-43 | 23-175 |
| ALT (U/L) | 20-44 | 16*-56 (#6863) | 15*-55 (#6894) | 18-204 |
| TBIL (mg/dL) | 0.1-0.2 | 0.2-0.4 | 0.1-0.2 | 0.1-0.6 |

Note:
Outside of normal range*

For all Groups, there was no significant change in weight over the course of the study (data not shown).

Overall the results indicate that Synthetic Consensus Survivin administered alone is capable of inducing an immune response in 100% of NHPs. The addition of IL-12 adjuvant improved the response noted for Synthetic Consensus Survivin, resulting in a much earlier, greater response PD2 but only with the higher dose of IL-12.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modification to the disclosed embodiments, including without limitation those relating to the chemical structures, substituents, derivatives, intermediates, syntheses, compositions, formulations, or methods of use of the invention, may be made without departing from the spirit and scope thereof.

What is claimed is:

1. A nucleic acid molecule comprising one or more nucleic acid sequences selected from the group consisting of:
   (a) a nucleic acid sequence that encodes SEQ ID NO:11;
   (b) a nucleic acid sequence that encodes SEQ ID NO:12;
   (c) a nucleic acid sequence that encodes SEQ ID NO:13;
   (d) a nucleic acid sequence that encodes a protein that is at least 95% identical to SEQ ID NO:11 and comprises SEQ ID NO: 5 and alanine at positions 33, 47, and 83 relative to SEQ ID NO: 11;
   (e) a nucleic acid sequence that encodes a protein that is at least 95% identical to SEQ ID NO:12 and comprises SEQ ID NO: 5 and alanine at positions 33, 47, and 83 relative to SEQ ID NO: 12; and
   (f) a nucleic acid sequence that encodes a protein that is at least 95% identical to SEQ ID NO: 13 and comprises SEQ TD NO: 5 and alanine at positions 33, 47, and 83 relative to SEQ ID NO: 13.

2. A nucleic acid molecule comprising one or more nucleic acid sequences selected from the group consisting of:
   (a) a nucleic acid sequence that encodes SEQ ID NO:2;
   (b) a nucleic acid sequence that encodes SEQ ID NO:4;
   (c) a nucleic acid sequence that encodes SEQ ID NO: 8;
   (d) a nucleic acid sequence that encodes a protein that is at least 95% identical to SEQ ID NO:2 and comprises SEQ ID NO: 5 and alanine at positions 51, 65, and 101 relative to SEQ ID NO: 2;
   (e) a nucleic acid sequence that encodes a protein that is at least 95% identical to SEQ ID NO:4 and comprises SEQ ID NO: 5 and alanine at positions 51, 65, and 101 relative to SEQ ID NO: 4; and
   (f) a nucleic acid sequence that encodes a protein that is at least 9500 identical to SEQ ID NO:8 and comprises SEQ TD NO: 5 and alanine at positions 51, 65, and 101 relative to SEQ ID NO: 8.

* * * * *